United States Patent
Morimoto et al.

(10) Patent No.: US 10,278,628 B2
(45) Date of Patent: May 7, 2019

(54) LIGHT SOURCE DEVICE FOR ENDOSCOPE AND ENDOSCOPE SYSTEM

(71) Applicant: FUJIFILM Corporation, Tokyo (JP)

(72) Inventors: Yoshinori Morimoto, Ashigarakami-gun (JP); Satoshi Ozawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 732 days.

(21) Appl. No.: 14/839,476

(22) Filed: Aug. 28, 2015

(65) Prior Publication Data

US 2016/0058349 A1   Mar. 3, 2016

(30) Foreign Application Priority Data

Aug. 29, 2014 (JP) .................................. 2014-175534

(51) Int. Cl.
*A61B 5/1455* (2006.01)
*A61B 5/1459* (2006.01)
*A61B 1/00* (2006.01)
*A61B 1/06* (2006.01)

(52) U.S. Cl.
CPC ........ *A61B 5/1459* (2013.01); *A61B 1/00009* (2013.01); *A61B 1/0638* (2013.01); *A61B 1/0646* (2013.01); *A61B 1/0669* (2013.01); *A61B 5/14551* (2013.01)

(58) Field of Classification Search
CPC . A61B 1/00009; A61B 1/0638; A61B 5/0059; A61B 5/1455; A61B 5/14551; A61B 5/14552; A61B 1/00165; A61B 1/0052; A61B 1/0661; A61B 5/0031; A61B 5/073; A61B 5/1459; A61B 5/6861
See application file for complete search history.

(56) References Cited

U.S. PATENT DOCUMENTS

| | | | | |
|---|---|---|---|---|
| 5,735,800 | A | * | 4/1998 | Yasukawa .......... A61B 5/02438 600/310 |
| 6,110,106 | A | * | 8/2000 | MacKinnon ......... A61B 5/0071 600/160 |
| 6,537,211 | B1 | * | 3/2003 | Wang ................. A61B 1/00009 600/160 |

(Continued)

FOREIGN PATENT DOCUMENTS

JP    5303012 B2    10/2013
JP    5306447 B2    10/2013

*Primary Examiner* — Eric F Winakur
*Assistant Examiner* — Chu Chuan Liu
(74) *Attorney, Agent, or Firm* — Birch, Stewart, Kolasch & Birch, LLP

(57) ABSTRACT

A band limiter comprises an optical filter, which has first and second filter sections, and a filter moving mechanism for moving the optical filter. The first filter section reduces intensity of blue light, which is emitted from a B-LED, in a wavelength range of greater than or equal to a peak wavelength of the blue light to generate first blue light. The second filter section reduces intensity of the blue light in a wavelength range of less than or equal to the peak wavelength of the blue light to generate second blue light. A light source controller places the first filter section in a light path of the blue light in a normal mode to generate the first blue light, and places the second filter section in the light path of the blue light in an oxygen saturation mode to generate the second blue light.

13 Claims, 15 Drawing Sheets

(56) References Cited

U.S. PATENT DOCUMENTS

2011/0288387 A1    11/2011  Machida et al.
2012/0116192 A1*   5/2012   Saito .................. A61B 1/00009
                                                        600/323
2012/0157768 A1    6/2012   Saito
2012/0176486 A1*   7/2012   Maeda ............... A61B 1/00009
                                                        348/68

* cited by examiner

LIGHT SOURCE DEVICE FOR ENDOSCOPE AND ENDOSCOPE SYSTEM

CROSS-REFERENCE TO RELATED APPLICATIONS

The present application claims priority under 35 U.S.C. § 119 to Japanese Patent Application No. 2014-175534, filed Aug. 29, 2014. Each of the above application(s) is hereby expressly incorporated by reference, in its entirety, into the present application.

BACKGROUND OF THE INVENTION

1. Field of the Invention

The present invention relates to a light source device for an endoscope and an endoscope system.

2. Description Related to the Prior Art

In medical fields, diagnoses using endoscope systems are widely performed. The endoscope system comprises a light source device for an endoscope (hereinafter simply referred to as the light source device), an endoscope, and a processor device. The light source device generates illumination light with which an object of interest (hereinafter simply referred to as the object, e.g. mucosa or the like in a body cavity) is to be irradiated. Observation modes of the endoscope system offer normal observation, in which normal light (white light) is used as the illumination light, and various types of special observation, in which special light is used as the illumination light. The observation of oxygen saturation levels (hereinafter referred to as the oxygen saturation observation) is one form of the special observation.

The oxygen saturation observation is a method of observation in which oxygen saturation levels, which indicate how much oxygen is contained in blood vessels, are calculated and an image representing the oxygen saturation levels is displayed. The oxygen saturation observation is performed by using light (measurement light) whose wavelength range is limited to 450 to 500 nm based on the fact that a difference between the absorption coefficients of oxyhemoglobin and deoxyhemoglobin, which are contained in blood vessels, is large in the wavelength range of 450 to 500 nm (see US2012/0157768 (corresponding to Japanese Pat. No. 5303012)).

It has been suggested to reduce the intensity of the normal light (the white light) in a wavelength range of 460 to 500 nm to prevent the reduction in contrast (hereinafter referred to as the blood vessel contrast) between the mucosal surface and the blood vessels in the normal observation. This is based on the fact that a difference in reflectance between the blood vessel and the mucosa surrounding the blood vessel is small in the wavelength range greater than or equal to 460 nm (see US2011/0288387 (corresponding to Japanese Pat. No. 5306447)). Thereby, the blood vessel contrast in the image is increased.

A broadband light source such as a xenon lamp, a white LED (Light Emitting Diode), or the like is used as the light source device. Recently, a combination of semiconductor light sources of different colors (e.g. a blue LED, a green LED, and a red LED) has been used. A blue LED having a peak wavelength around 450 to 460 nm is used as a blue light source.

As described in the US2012/0157768 and the US2011/0288387, the illumination light in the wavelength range of 450 to 500 nm is used for the oxygen saturation observation, whereas the intensity of the illumination light in the wavelength range of 460 to 500 nm is reduced in the normal observation to increase the blood vessel contrast. In other words, the blue illumination light for the normal observation differs in wavelength from that for the oxygen saturation observation. For this reason, it is necessary to use different light sources for the normal observation and the oxygen saturation observation, respectively. The two types of observation cannot be performed by using a single endoscope system.

SUMMARY OF THE INVENTION

An object of the present invention is to provide a light source device for endoscope and an endoscope system that allow both of normal observation using an image in which the contrast of blood vessels is enhanced and observation of oxygen saturation level.

In order to achieve the above and other objects, an aspect of the present invention provides a light source device for an endoscope comprising a blue light source for emitting blue light, a band limiter, and a light source controller. The band limiter selectively generates first blue light and second blue light from the blue light emitted from the blue light source. The band limiter reduces intensity of the blue light in a wavelength range of at least greater than or equal to a peak wavelength of the blue light to generate the first blue light. The band limiter reduces intensity of the blue light in a wavelength range of at least less than or equal to the peak wavelength of the blue light to generate the second blue light. The light source controller controls the blue light source and the band limiter, to allow generating the first blue light as first illumination light and the second blue light as second illumination light.

It is preferred that the peak wavelength of the blue light is greater than or equal to 450 nm. It is preferred that the peak wavelength of the blue light is within a range of 450 to 460 nm.

It is preferred that the band limiter comprises an optical filter and a filter moving mechanism. The optical filter comprises a first filter section for generating the first blue light from the blue light and a second filter section for generating the second blue light from the blue light. The filter moving mechanism moves the optical filter to place one of the first and second filter sections in a light path of the blue light.

The band limiter may comprise a dichroic mirror, a light shielding plate, and a light shielding plate moving mechanism. The dichroic mirror separates the blue light into the first blue light and the second blue light. The light shielding plate blocks the blue light. The light shielding plate moving mechanism moves the light shielding plate to place the light shielding plate in one of light paths of the first blue light and the second blue light.

The band limiter may comprise a dichroic mirror, a first transmittance changing unit, a second transmittance changing unit, and a transmittance controller. The dichroic mirror separates the blue light into the first blue light and the second blue light. The first transmittance changing unit has variable transmittance and reduces intensity of the first blue light. The second transmittance changing unit has variable transmittance and reduces intensity of the second blue light. The transmittance controller controls the transmittance of the first transmittance changing unit and the transmittance of the second transmittance changing unit.

It is preferred that the light source device further comprises a green light source for emitting green light and a red light source for emitting red light. It is preferred that the light source controller allows generating the first illumination light and the second illumination light. The first illumination light contains the first blue light, the green light, and the red light. The second illumination light contains the second blue light.

An aspect of the present invention provides an endoscope system comprising the above-described light source device for the endoscope, an imaging unit, and an image processing unit. The imaging unit images an object of interest irradiated with the first or second illumination light and outputs an image signal. The image processing unit produces a first image based on the image signal obtained by imaging the object of interest irradiated with the first illumination light. The image processing unit produces a second image based on the image signal obtained by imaging the object of interest irradiated with the second illumination light.

It is preferred that the endoscope system further comprises a display unit for displaying the first image and the second image. It is preferred that the display unit displays the first and second images simultaneously.

It is preferred that the second blue light has a wavelength range in which an absorption coefficient of oxyhemoglobin is greater than an absorption coefficient of deoxyhemoglobin.

It is preferred that the imaging unit has blue pixels for receiving the blue light, green pixels for receiving the green light, and red pixels for receiving the red light.

It is preferred that the image processing unit images the object of interest irradiated with the first illumination light and produces the first image based on a first blue image signal outputted from the blue pixels, a first green image signal outputted from the green pixels, and a first red image signal outputted from the red pixels.

It is preferred that the second illumination light is separated into normal light and measurement light. The normal light contains the second blue light, the green light, and the red light. The measurement light is composed of the second blue light. It is preferred that the image processing unit images the object of interest irradiated with the normal light and produces a base image based on a second blue image signal outputted from the blue pixels, a second green image signal outputted from the green pixels, and a second red image signal outputted from the red pixels. It is preferred that the image processing unit images the object of interest irradiated with the measurement light and calculates the oxygen saturation level based on a third blue image signal outputted from the blue pixels, and performs image processing of the base image based on the oxygen saturation level to produce the second image.

It is preferred that the endoscope system further comprises a violet light source for emitting violet light to which the blue pixels are sensitive. It is preferred that the light source controller generates the first illumination light containing the violet light, the first blue light, the green light, and the red light.

It is preferred that the endoscope system is capable of executing a normal mode in which the object of interest is irradiated only with the first illumination light and only the first image is produced.

According to an aspect of the present invention, the light source device comprises the band limiter that selectively generates the first blue light and the second blue light from the blue light emitted from the blue light source. The intensity of the blue light in the wavelength range of at least greater than or equal to the peak wavelength of the blue light is reduced to generate the first blue light. The intensity of the blue light in the wavelength range of at least less than or equal to the peak wavelength of the blue light is reduced to generate the second blue light. Thereby, the present invention allows both the normal observation of an image in which the blood vessel contrast is enhanced and the observation of oxygen saturation level.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

First Embodiment

Figure 1:
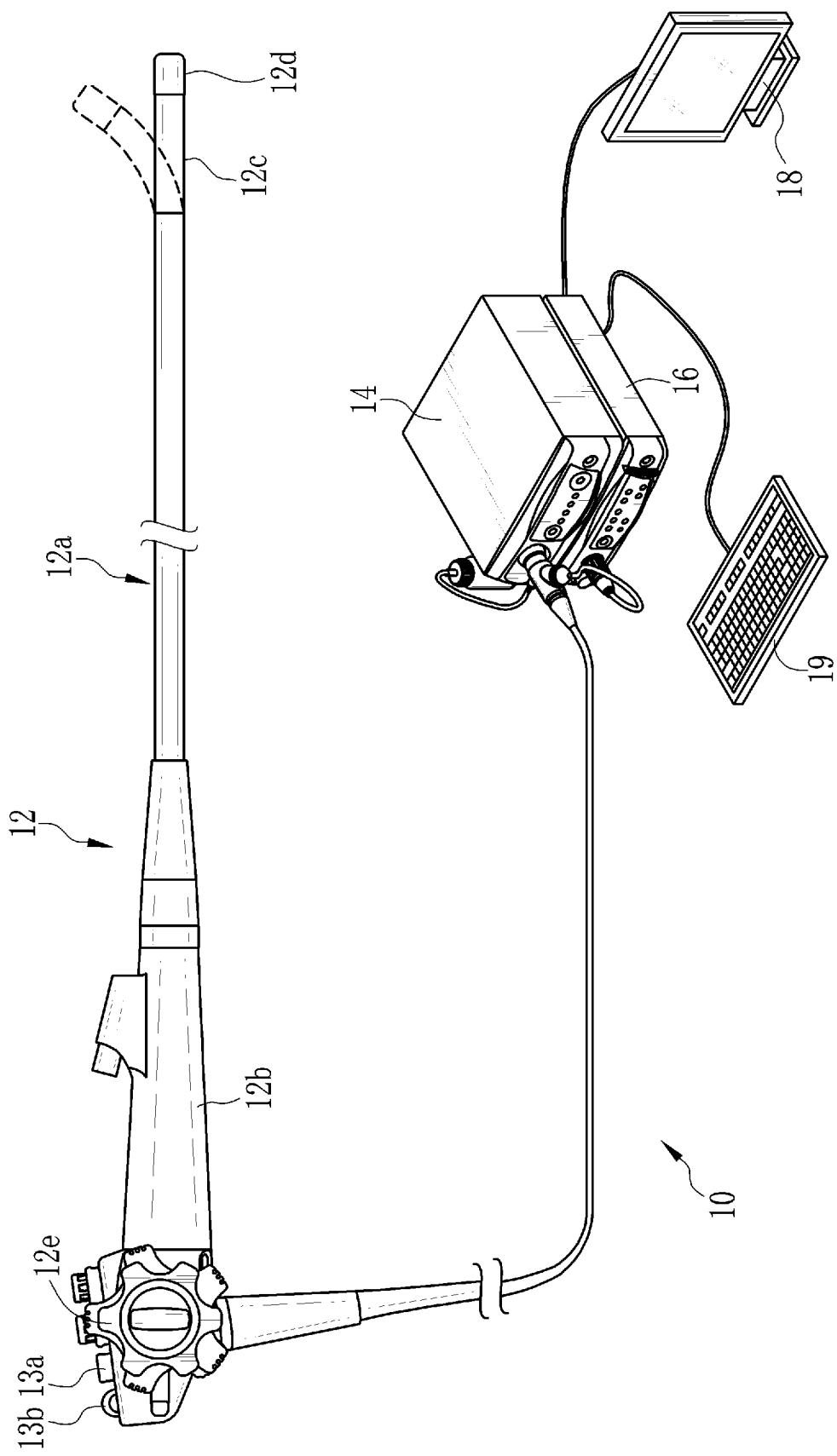
FIG. 1 is an external view of an endoscope system.

In FIG. 1, an endoscope system 10 comprises an endoscope 12, a light source device 14 for an endoscope (hereinafter simply referred to as the light source device 14), a processor device 16, a monitor 18, and a console 19. The endoscope 12 is connected optically to the light source device 14 and electrically to the processor device 16. The endoscope 12 comprises an insertion section 12a to be inserted into a body cavity, a control handle unit 12b provided at the proximal end of the insertion section 12a, a flexible portion 12c, and a distal portion 12d. The distal portion 12d is coupled to the flexible portion 12c, which is provided on the distal side of the insertion section 12a. The flexible portion 12c is bent by operating an angle knob 12e of the control handle unit 12b. The distal portion 12d is directed to a desired direction by bending the flexible portion 12c.

The control handle unit 12b is provided with the angle knob 12e, a mode switch (SW) 13a, and a zoom operating section 13b. The mode SW 13a is operated to switch between observation modes. The endoscope system 10 is capable of executing a normal mode and an oxygen saturation mode.

In the normal mode, the monitor 18 (a display unit) displays a white light image (hereinafter referred to as the normal image) in which the contrast of blood vessels (hereinafter referred to as the blood vessel contrast) in mucosal surface of living tissue is enhanced. In the oxygen saturation mode, the monitor 18 displays an oxygen saturation image. The oxygen saturation image refers to an image with colors corresponding to values of oxygen saturation levels measured by irradiating an object of interest (hereinafter simply referred to as the object) with measurement light. The measurement light has a specific wavelength range for measuring the oxygen saturation levels.

The processor device 16 is electrically connected to the monitor 18 and the console 19. The monitor 18 outputs and displays image(s) and image information and the like associated with the image(s) in each mode. The console 19 functions as a UI (user interface), which receives input operation such as setting a function. Note that an external storage unit (not shown) for recording the images and the image information may be connected to the processor device 16.

Figure 2:
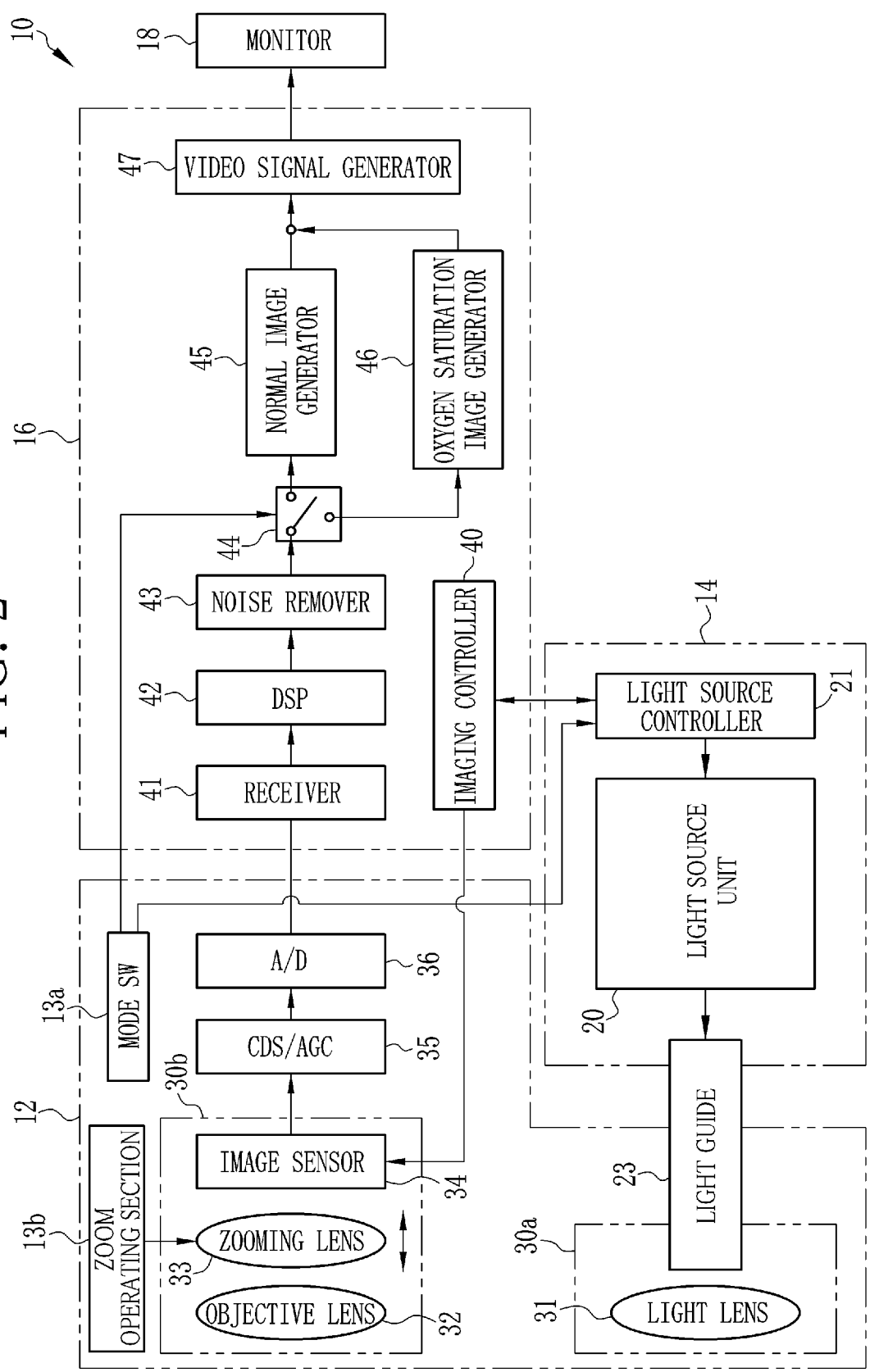
FIG. 2 is a block diagram illustrating functions of an endoscope system.

As illustrated in FIG. 2, the light source device 14 comprises a light source unit 20 and a light source controller 21. The light source unit 20 generates illumination light with which the object is to be irradiated. The light source controller 21 controls the operation of the light source unit 20. The light source unit 20 generates first illumination light in the normal mode and second illumination light in the oxygen saturation mode.

Figure 4:
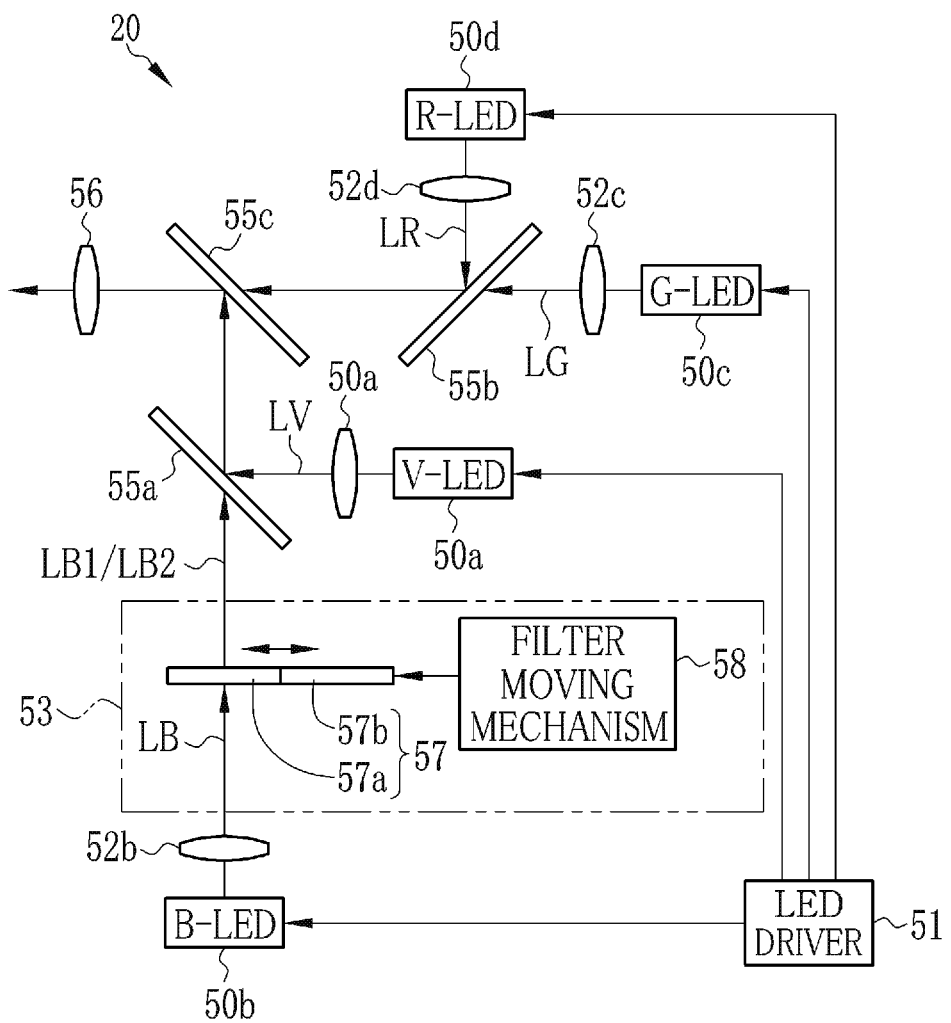
FIG. 4 is a schematic view of a light source device.

The first and second illumination light enters a light guide 23, which extends through the insertion section 12a, through a condenser lens 56 (see FIG. 4). The light guide 23 is incorporated in the endoscope 12 and transmits the first and second illumination light to the distal portion 12d of the endoscope 12. Note that a multimode fiber may be used as the light guide 23. For example, a small-diameter fiber cable with the core diameter 105 µm, the clad diameter 125 µm, and the outer diameter φ0.3 to 0.5 mm (including a protection layer, being a jacket) may be used.

The distal portion 12d of the endoscope 12 comprises an illumination optical system 30a and an imaging optical system 30b. The illumination optical system 30a has a light lens 31. The first and second illumination light transmitted through the light guide 23 is applied to the object through the light lens 31. The imaging optical system 30b has an objective lens 32, a zooming lens 33, and an image sensor (an imaging unit) 34. The light reflected from the object is incident on the image sensor 34 through the objective lens 32 and the zooming lens 33. An image of the light reflected from the object is formed on the image sensor 34. Note that the zooming lens 33 is moved as desired between the telephoto end and the wide angle end by operating the zoom operating section 13b, to magnify or reduce the size of the light image of the object formed on the image sensor 34.

The image sensor 34 is a color image sensor. The image sensor 34 captures the light image of the object, and outputs an image signal. It is preferred that the image sensor 34 is a CCD (Charge Coupled Device) image sensor, a CMOS (Complementary Metal-Oxide Semiconductor) image sensor, or the like.

Figure 3:
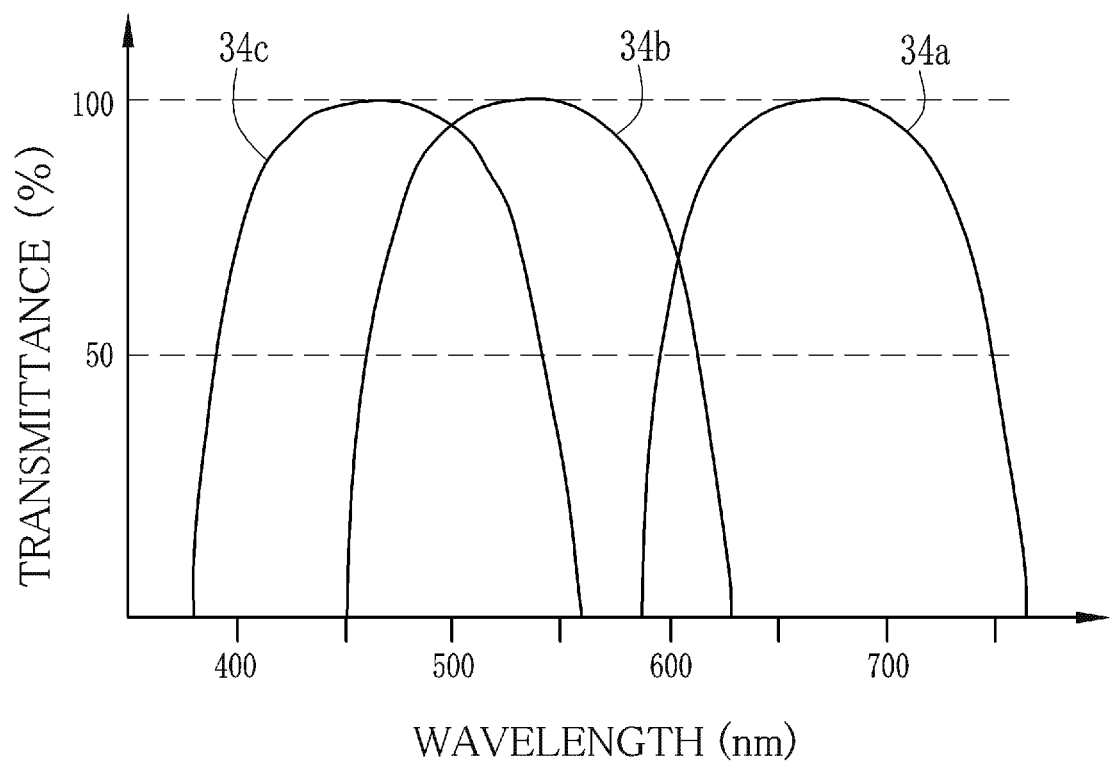
FIG. 3 illustrates spectral characteristics of color filters.

The image sensor 34 comprises red (R) color filters each having first spectral transmittance 34a, green (G) color filters each having second spectral transmittance 34b, and blue (B) color filters each having third spectral transmittance 34c (see FIG. 3). Each pixel is provided with one of the color filters. In other words, the image sensor 34 has R (red) pixels provided with the R color filters, G (green) pixels provided with the G color filters, and B (blue) pixels provided with the B color filters, and outputs RGB image signals. Each pixel is assigned one of RGB color signals to generate the RGB image signals. Note that the B pixels are sensitive to violet light and blue light.

The image signal outputted from the image sensor 34 is transmitted to a CDS/AGC circuit 35. The CDS/AGC circuit 35 performs correlated double sampling (CDS) and automatic gain control (AGC) on the image signal, being an analog signal. The image signal that is outputted from the CDS/AGC circuit 35 is then converted into a digital image signal by an A/D converter 36. The digital image signal is inputted to the processor device 16.

The processor device 16 comprises an imaging controller 40, a receiver 41, a DSP (Digital Signal Processor) 42, a noise remover 43, an image processing selector 44, a normal image generator 45, an oxygen saturation image generator 46, and a video signal generator 47. For example, the normal image generator 45 and the oxygen saturation image generator 46 correspond to an image processor described in claims.

The imaging controller 40 controls timing of imaging the object with the image sensor 34 and timing of outputting the image signals from the image sensor 34. The receiver 41 receives the digital RGB image signals from the endoscope 12. The DSP 42 performs various types of signal processing (defect correction process, offset processing, gain correction process, linear matrix processing, gamma conversion process, demosaicing process, and the like) on the image signal received.

In the defect correction process, signals from defective pixels in the image sensor 34 are corrected. In the offset processing, dark current components are removed from the RGB image signals that have been subjected to the defect correction process. Thereby an accurate zero level is set. In the gain correction process performed after the offset processing, a signal level is adjusted or corrected by multiplying the RGB image signals by a specific gain. After the gain correction process, the RGB image signals are subjected to the linear matrix processing to increase color reproducibility. Thereafter, brightness and saturation are adjusted or corrected through the gamma conversion process. After the linear matrix processing, the RGB image signals are subjected to the demosaicing process (also referred to as equalization process or synchronization process), in which color signal(s) lacking in each pixel is generated by interpolation. Owing to the demosaicing process, each pixel has the color signals of three colors (RGB).

The DSP 42 performs the demosaicing process and the like on the RGB image signals. Thereafter, the noise remover 43 removes noise from the RGB image signals through a noise removing process (for example, moving average method or median filter method). Then, the RGB image signals are inputted to the image processing selector 44. The image processing selector 44 is controlled by the mode SW 13a. In a case where the mode is set to the normal mode, the image processing selector 44 outputs the RGB image signals to the normal image generator 45. In a case where the mode is set to the oxygen saturation mode, the image processing selector 44 outputs the RGB image signals to the oxygen saturation image generator 46.

The normal image generator 45 operates in a case where the observation mode is set to the normal mode, and performs a color conversion process, a color enhancement process, and a structure enhancement process on the RGB image signals to produce the normal image (first image). The color conversion process is performed on the RGB image signals through 3×3 matrix processing, a tone conversion process, a three-dimensional LUT process, and the like. The color enhancement process is performed on the RGB image signals that have been subjected to the color conversion process. The structure enhancement process is to enhance the structure of the object (e.g. surface blood vessels, pit patterns, or the like). The structure enhancement process is performed on the RGB image signals that have been subjected to the color enhancement process.

The oxygen saturation image generator 46 operates in a case where the observation mode is set to the oxygen saturation mode. Based on the RGB image signals, the oxygen saturation image generator 46 calculates the oxygen saturation level and produces the oxygen saturation image (second image).

The normal image produced by the normal image generator 45 and the oxygen saturation image produced by the oxygen saturation image generator 46 are inputted to the video signal generator 47. The video signal generator 47 converts each image into a video signal to be displayed on the monitor 18. Based on the video signal inputted from the video signal generator 47, the monitor 18 displays the normal image and/or the oxygen saturation image.

In FIG. 4, the light source unit 20 comprises a V-LED (Violet Light Emitting Diode) 50a, a B-LED (Blue Light Emitting Diode) 50b, a G-LED (Green Light Emitting Diode) 50c, an R-LED (Red Light Emitting Diode) 50d, an LED driver 51, first to fourth collimator lenses 52a to 52d, a band limiter 53, first to third dichroic mirrors (DM) 55a to 55c, and the condenser lens 56.

The V-LED 50a is a violet light source that emits violet light LV having a wavelength range of 380 to 420 nm and a peak wavelength 405 nm. The B-LED 50b is a blue light source that emits blue light LB having a wavelength range of 420 to 500 nm and a peak wavelength 460 nm. The G-LED 50c is a green light source that emits green light LG having a wavelength range of 480 to 600 nm. The R-LED 50d is a red light source that emits red light LR having a wavelength range of 600 to 650 nm and the center wavelength 620-630 nm.

Figure 5:
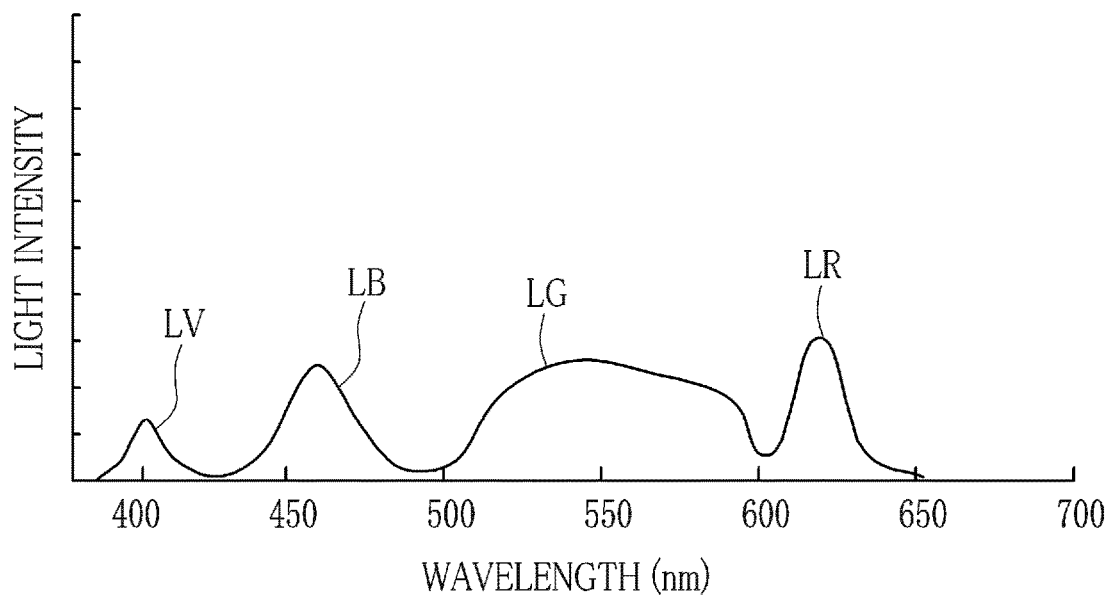
FIG. 5 is a graph illustrating an optical spectrum of violet light, blue light, green light, and red light.

The LED driver 51 independently drives the V-LED 50a, the B-LED 50b, the G-LED 50c, and the R-LED 50d. The emission intensity spectrums of the respective violet light LV, the blue light LB, the green light LG, and the red light LR are distributed as illustrated in FIG. 5. Note that each of the peak wavelengths of the violet light LV and the blue light LB has a wavelength width in the order of ±5 nm to ±10 nm.

The first to fourth collimator lenses 52a to 52d are disposed to correspond to the V-LED 50a, the B-LED 50b, the G-LED 50c, and the R-LED 50d to collimate the violet light LV, the blue light LB, the green light LG, and the red light LR, respectively.

The band limiter 53 comprises an optical filter 57 and a filter moving mechanism 58. The optical filter 57 is disposed in a light path of the blue light LB emitted from the B-LED 50b. To be more specific, the optical filter 57 comprises a first filter section 57a and a second filter section 57b. One of the first filter section 57a and the second filter section 57b is placed in the light path of the blue light LB.

Figure 6:
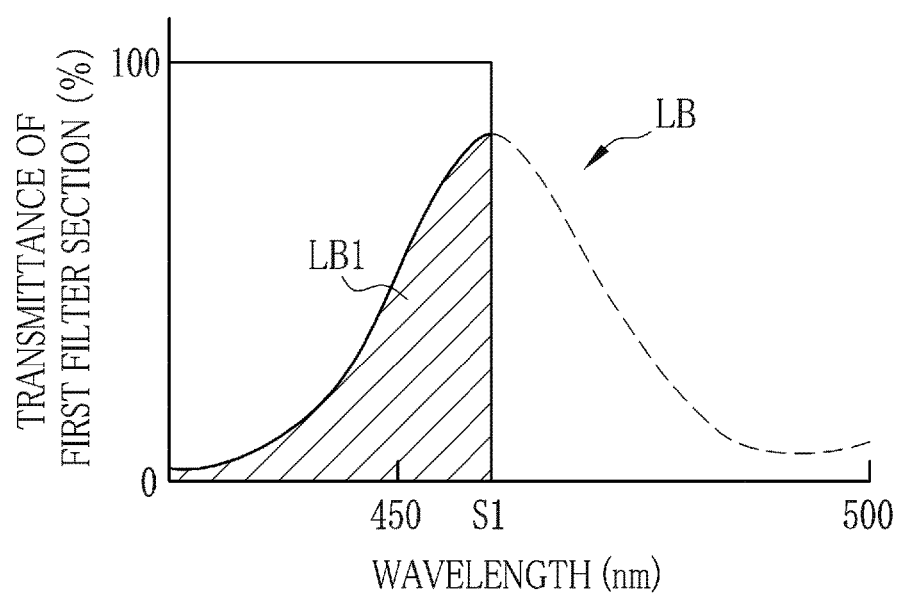
FIG. 6 is a graph illustrating an optical characteristic of a first filter section.

FIG. 6 illustrates the optical characteristics of the first filter section 57a. As illustrated in FIG. 6, the transmittance to light in a wavelength range greater than or equal to a threshold value S1 is approximately 0%. The transmittance to light in a wavelength range less than the threshold value S1 is approximately 100%. Here, the threshold value S1 substantially equals the peak wavelength 460 nm of the blue light LB. The first filter section 57a reduces the intensity of the blue light LB in a wavelength range greater than or equal to the peak wavelength of the blue light LB, to generate first blue light LB1 that is a short wavelength component of the blue light LB.

Figure 7:
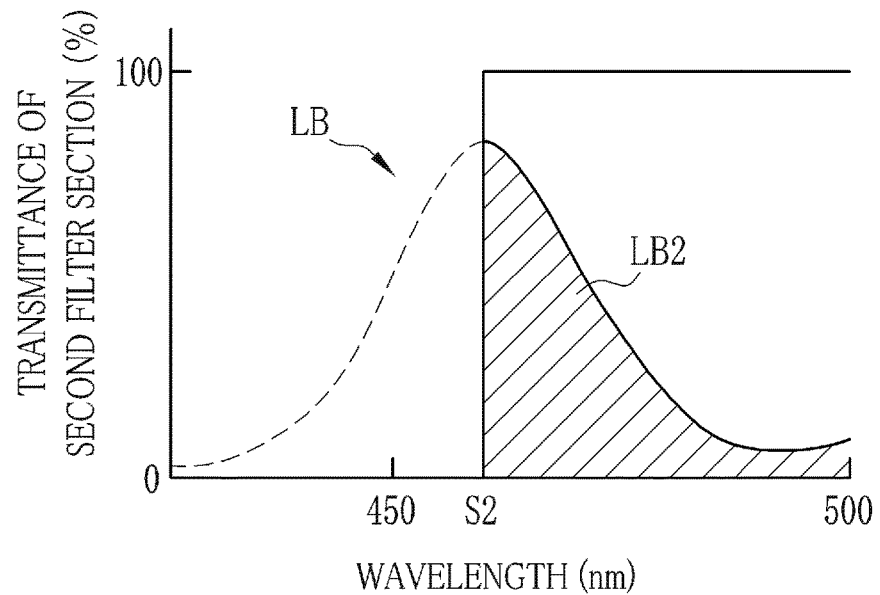
FIG. 7 is a graph illustrating an optical characteristic of a second filter section.

FIG. 7 illustrates the optical characteristics of the second filter section 57b. As illustrated in FIG. 7, the transmittance to light in a wavelength range less than or equal to a threshold value S2 is approximately 0%. The transmittance to light in a wavelength range greater than the threshold value S2 is approximately 100%. Here, the threshold value S2 substantially equals the peak wavelength 460 nm of the blue light LB. The second filter section 57b reduces the intensity of the blue light LB in a wavelength range less than or equal to the peak wavelength of the blue light LB, to generate second blue light LB2 that is a long wavelength component of the blue light LB.

The filter moving mechanism 58 linearly moves or slides the optical filter 57 in a direction orthogonal to the light path of the blue light LB, thereby placing one of the first filter section 57a and the second filter section 57b in the light path of the blue light LB.

Figure 8:
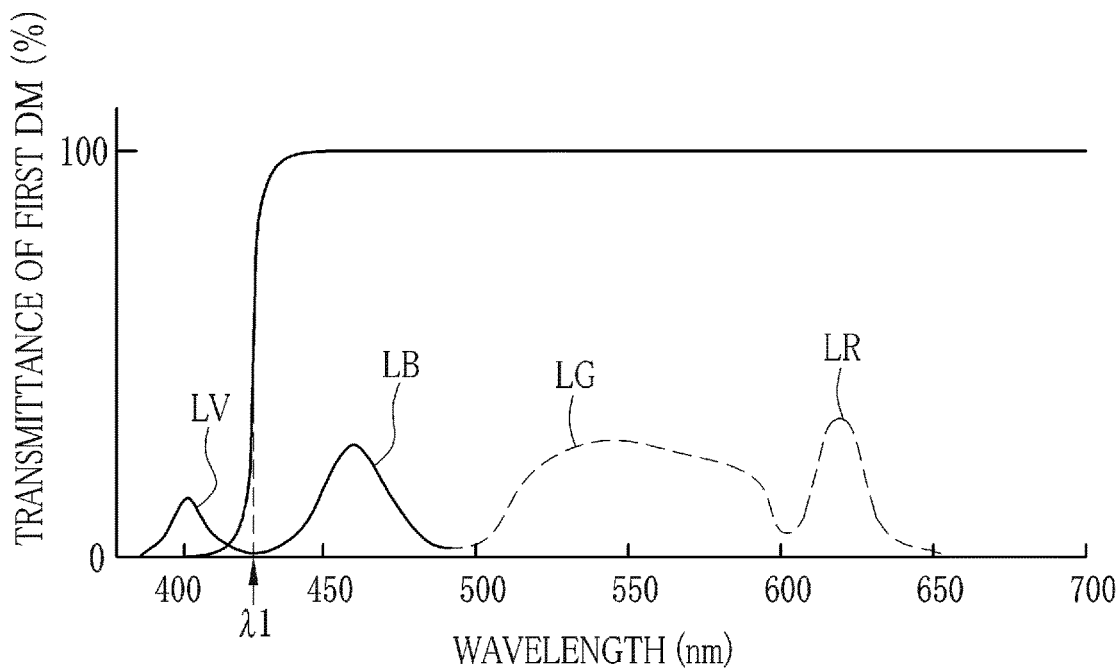
FIG. 8 is a graph illustrating an optical characteristic of a first dichroic mirror.

As illustrated in FIG. 4, the light path of the blue light LB (the first blue light LB1 or the second blue light LB2) that has passed through the optical filter 57 is orthogonal to the light path of the violet light LV, and the first DM 55a is disposed at the intersection of the light path of the blue light LB and the light path of the violet light LV. To be more specific, the first DM 55a is disposed such that the first blue light LB1 or the second blue light LB2 is incident on one of its surfaces at the angle of 45° (degrees) and the violet light LV is incident on the other surface at the angle of 45°. As illustrated in FIG. 8, the first DM 55a has a threshold value λ1 of approximately 425 nm. The first DM 55a passes the light with the wavelengths longer than the threshold value λ1 and reflects the light with the wavelengths shorter than the threshold value λ1. Thereby, the first DM 55a combines the light path of the blue light LB that has passed the optical filter 57 with the light path of the violet light LV.

Figure 9:
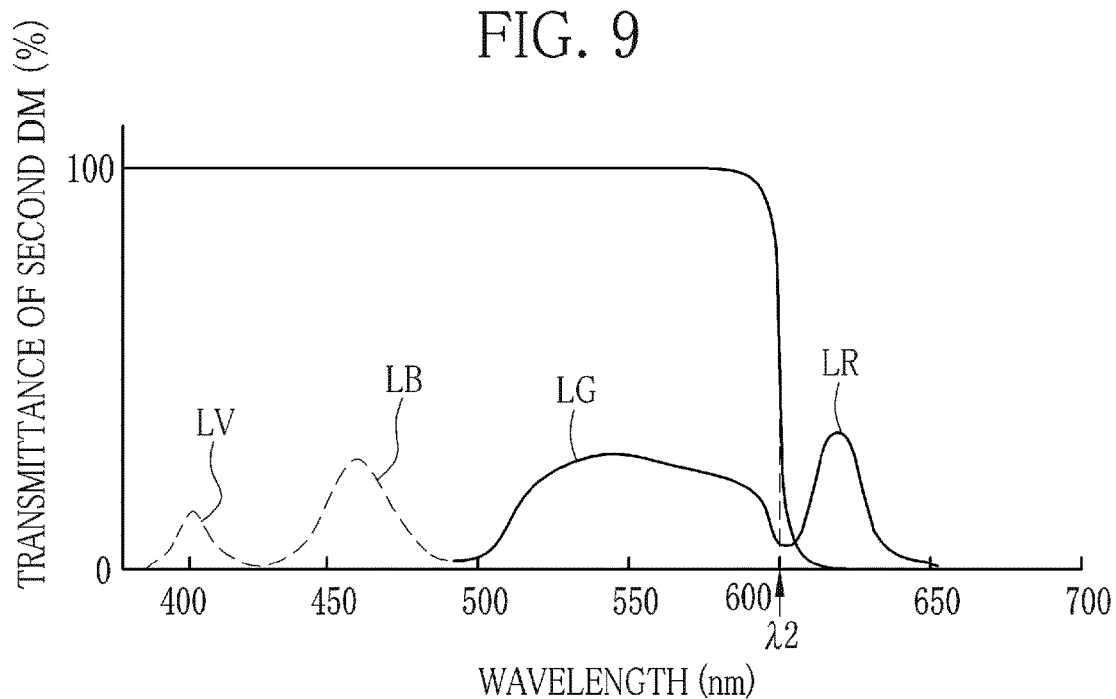
FIG. 9 is a graph illustrating an optical characteristic of a second dichroic mirror.

The light path of the green light LG emitted from the G-LED 50c is orthogonal to the light path of the red light LR emitted from the R-LED 50d, and the second DM 55b is disposed at the intersection of the light path of the green light LG and the light path of the red light LR. To be more specific, the second DM 55b is disposed such that the green light LG is incident on one of its surfaces at the angle of 45° and the red light LR is incident on the other surface at the angle of 45°. As illustrated in FIG. 9, the second DM 55b has a threshold value λ2 of approximately 600 nm. The second DM 55b passes the light with the wavelengths shorter than the threshold value λ2 and reflects the light with the wavelengths longer than the threshold value λ2. Thereby, the second DM 55b combines the light path of the green light LG with the light path of the red light LR.

Figure 10:
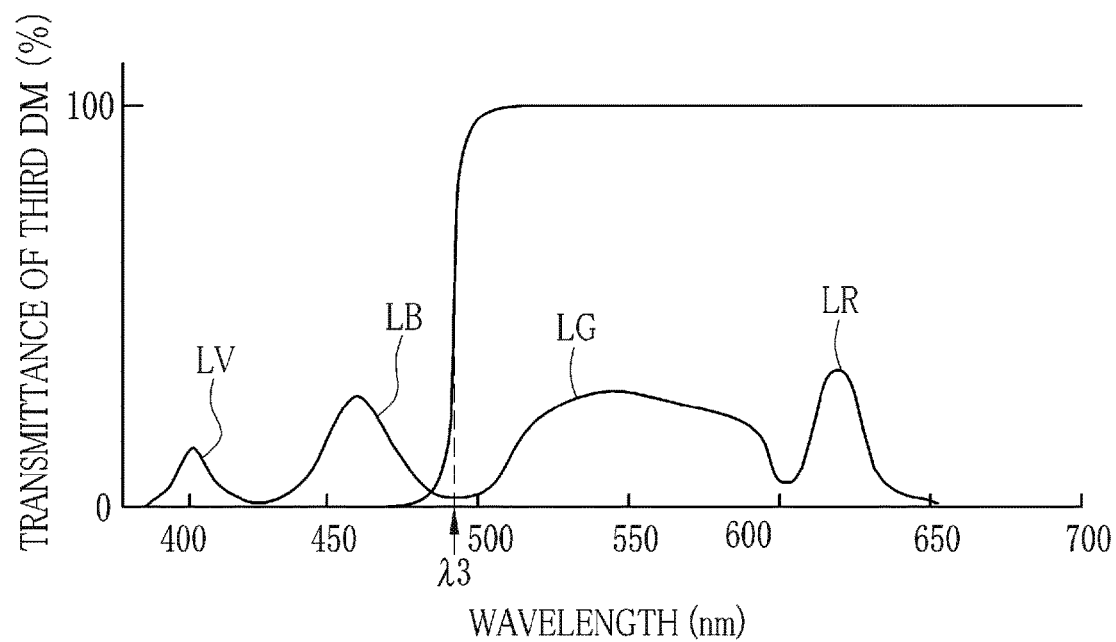
FIG. 10 is a graph illustrating an optical characteristic of a third dichroic mirror.

The light path of the blue light LB (the first blue light LB1 or the second blue light LB2) and the violet light LV that have been combined together by the first DM 55a is orthogonal to the light path of the green light LG and the red light LR that have been combined together by the second DM 55b, and the third DM 55c is disposed at the intersection thereof. To be more specific, the third DM 55c is disposed such that the blue light LB and the violet light LV are incident on one of its surfaces at the angle of 45° and the green light LG and the red light LR are incident on the other surface at the angle of 45°. As illustrated in FIG. 10, the third DM 55c has a threshold value λ3 of approximately 490 nm. The third DM 55c passes the light with the wavelengths longer than the threshold value λ3 and reflects the light with the wavelengths shorter than the threshold value λ3. Thereby, the third DM 55c combines the light path of the blue light LB and the violet light LV with the light path of the green light LG and the red light LR.

The condenser lens 56 is disposed in the proximity of an incident end of the light guide 23. The condenser lens 56 collects the light passed through and reflected from the third DM 55c and allows the collected light to enter the incident end of the light guide 23.

The LED driver 51 and the filter moving mechanism 58 are controlled by the light source controller 21 in accordance with the observation mode chosen. To be more specific, in the normal mode, the light source controller 21 controls the filter moving mechanism 58 to place the first filter section 57a of the optical filter 57 in the light path of the blue light LB. The light source controller 21 controls the LED driver 51 to turn on all of the V-LED 50a, the B-LED 50b, the G-LED 50c, and the R-LED 50d.

Figure 11:
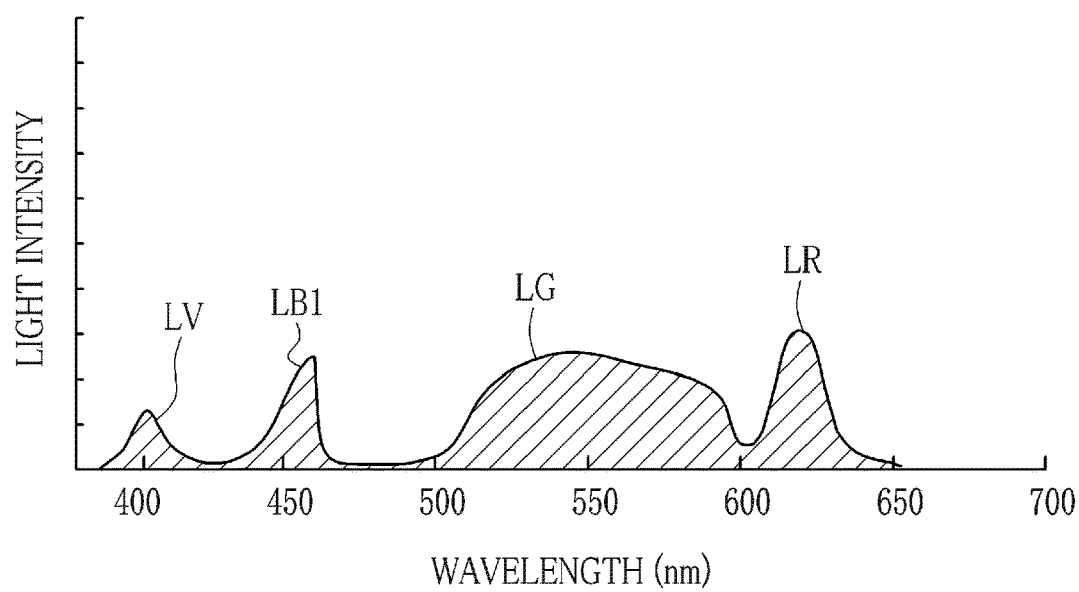
FIG. 11 is a graph illustrating an optical spectrum of first illumination light.

Thereby, in the normal mode, the light source unit 20 emits the first illumination light having a light intensity spectrum illustrated in FIG. 11. The first illumination light enters the light guide 23 through the condenser lens 56. The first illumination light is substantially the white light. In the normal mode, the first filter section 57a limits the wavelength range (or band) of the blue light LB to generate the first blue light LB1 because the light in the wavelength range of 460 to 500 nm reduces the contrast of the structure such as the surface blood vessels, the pit patterns, and the like.

The first filter section 57a reduces the intensity of the light in the wavelength range greater than or equal to the threshold value S1. Actually, the threshold value S1 has the wavelength width in the order of 5 to 10 nm. In a case where the threshold value S1 is 460 nm, the transmittance of the first filter section 57a starts to decrease at around the wavelength 450 nm. In order to maintain color rendering properties of the xenon light source, it is preferred that a discrete wavelength range does not exist in the optical spectrum of the illumination light applied to the object. For this reason, the first filter section 57a does not reduce the intensity of the light in the wavelength range greater than or equal to 460 nm to zero, but reduces the intensity of the light in the wavelength range greater than or equal to 460 nm such that the color rendering properties of the xenon light source is maintained. Therefore, as illustrated in FIG. 11, a discrete wavelength range does not exist in the first illumination light.

In the oxygen saturation mode, the light source controller 21 allows the light source unit 20 to emit the second illumination light. The second illumination light is separated into normal light and measurement light. In the oxygen saturation mode, the light source controller 21 controls the filter moving mechanism 58 to place the second filter section 57b of the optical filter 57 in the light path of the blue light LB, and allows alternately executing a first emission mode for emitting the normal light and a second emission mode for emitting the measurement light.

Figure 12:
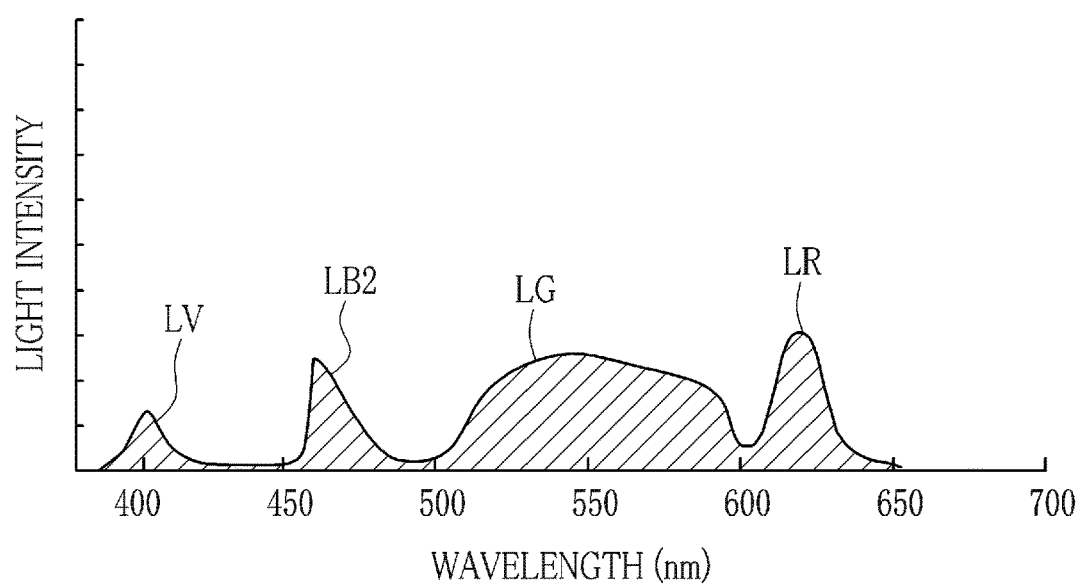
FIG. 12 is a graph illustrating an optical spectrum of normal light of second illumination light.

In the first emission mode, the second filter section 57b of the optical filter 57 is placed in the light path of the blue light LB and all of the V-LED 50a, the B-LED 50b, the G-LED 50c, and the R-LED 50d are turned on. In the normal mode, the normal light having the light intensity spectrum illustrated in FIG. 12 is emitted from the light source unit 20 and enters the light guide 23 through the condenser lens 56.

Figure 13:
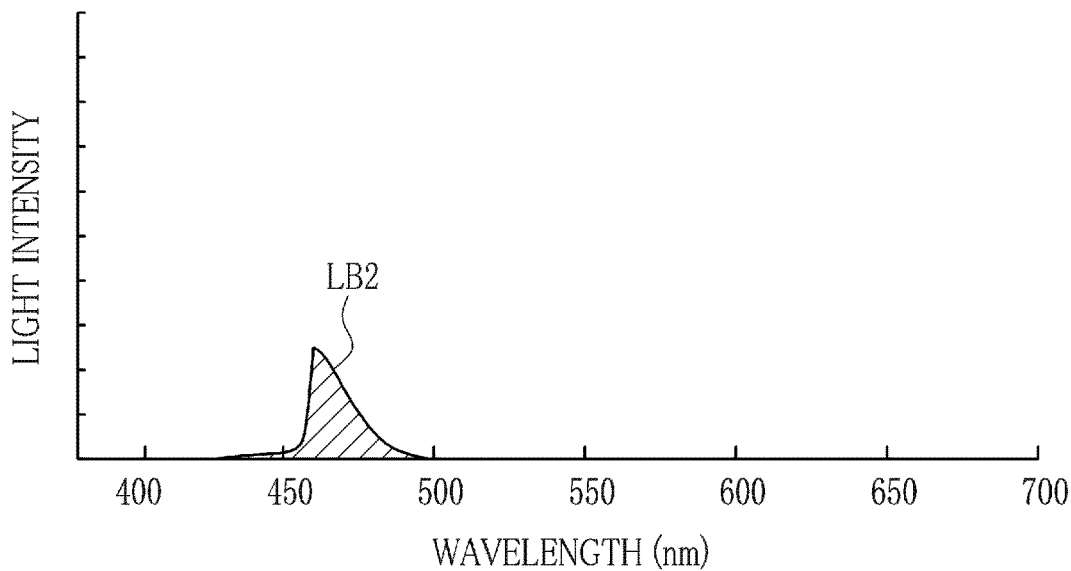
FIG. 13 is a graph illustrating an optical spectrum of measurement light of the second illumination light.

The second emission mode is used to measure the oxygen saturation level(s). In the second emission mode, the light source controller 21 controls the LED driver 51 to turn on the B-LED 50b and turn off the V-LED 50a, the G-LED 50c, and the R-LED 50d while the second filter section 57b of the optical filter 57 is placed in the light path of the blue light LB. Thereby, in the second emission mode, the measurement light having the light intensity spectrum illustrated in FIG. 13 is emitted from the light source unit 20 and enters the light guide 23 through the condenser lens 56.

As described above, in the normal mode, the first illumination light is applied to the object. The B pixels of the image sensor 34 receive the violet light LV and the first blue light LB1 that are reflected from the object, and output a B image signal. The G pixels of the image sensor 34 receive the green light LG reflected from the object, and output a G image signal. The R pixels of the image sensor 34 receive the red light LR reflected from the object, and output an R image signal. Hereinafter, the B image signal, the G image signal, and the R image signal obtained in the normal mode are referred to as the first blue image signal (the B1 image signal), the first green image signal (the G1 image signal), and the first red image signal (the R1 image signal).

In the oxygen saturation mode, the second illumination light is applied to the object. To be more specific, in the first emission mode of the oxygen saturation mode, the normal light is applied to the object. The B pixels of the image sensor 34 receive the violet light LV and the second blue light LB2 that are reflected from the object, and output a B image signal. The G pixels of the image sensor 34 receive the green light LG reflected from the object, and output a G image signal. The R pixels of the image sensor 34 receive the red light LR reflected from the object, and output an R image signal. Hereinafter, the B image signal, the G image signal, and the R image signal obtained in the first emission mode are referred to as the second blue image signal (B2 image signal), the second green image signal (G2 image signal), and the second red image signal (R2 image signal).

In the second emission mode in the oxygen saturation mode, the measurement light is applied to the object. The measurement light is composed of the second blue light LB2. The B pixels of the image sensor 34 receive the second blue light LB2 reflected from the object and output a B image signal. Hereinafter, the B image signal obtained in the second emission mode is referred to as the third blue image signal (B3 image signal). Note that the image sensor 34 is also capable of outputting the G and R image signals in the second emission mode. However, the G and R image signals are not used for calculating the oxygen saturation level and producing the oxygen saturation image. In this embodiment, the image sensor 34 outputs only the B3 image signal in the second emission mode.

The second blue light LB2 has a specific wavelength range for measuring the oxygen saturation level(s). The specific wavelength range refers to a wavelength range in which a difference between an absorption coefficient of oxyhemoglobin and an absorption coefficient of deoxyhemoglobin causes a difference in amount of light absorption in accordance with the oxygen saturation level.

Figure 14:
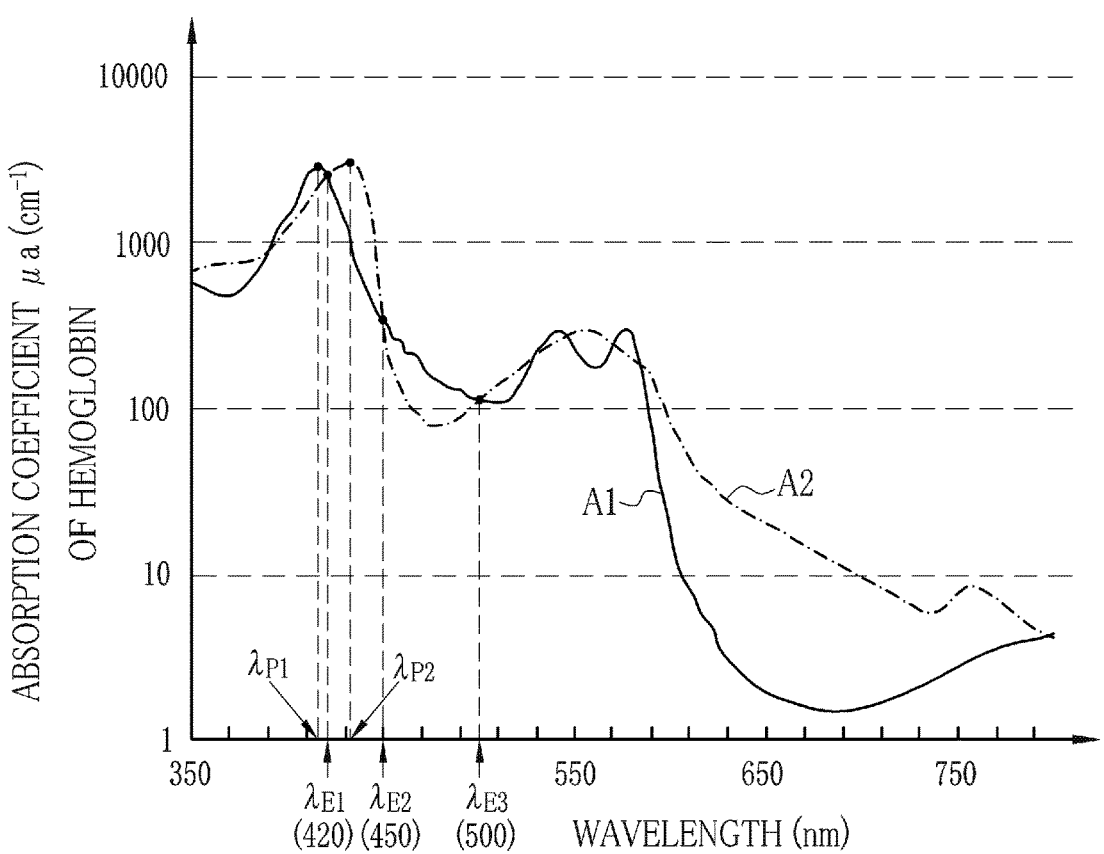
FIG. 14 is a graph illustrating wavelength dependence of absorption coefficients of oxyhemoglobin and deoxyhemoglobin.

As illustrated in FIG. 14, a magnitude relationship between an absorption coefficient A1 of oxyhemoglobin and an absorption coefficient A2 of deoxyhemoglobin varies depending on a wavelength range, and the absorption coefficient A1 of oxyhemoglobin equals (or crosses) the absorption coefficient A2 of deoxyhemoglobin at two or more wavelengths (isosbestic wavelengths). The wavelength at which the absorption coefficient A1 of oxyhemoglobin equals (or crosses) the absorption coefficient A2 of deoxyhemoglobin is referred to as the isosbestic wavelength. For example, there are first to third isosbestic wavelengths $\lambda_{E1}$ to $\lambda_{E3}$ in a wavelength range from violet to blue. The first to third isosbestic wavelengths $\lambda_{E1}$ to $\lambda_{E3}$ are approximately 420 nm, approximately 450 nm, and approximately 500 nm, respectively. A relationship A2>A1 is satisfied in a wavelength range (420 to 450 nm) between the first isosbestic wavelength $\lambda_{E1}$ and the second isosbestic wavelength $\lambda_{E2}$. A relationship A1>A2 is satisfied in a wavelength range (450 to 500 nm) between the second isosbestic wavelength $\lambda_{E2}$ and the third isosbestic wavelength $\lambda_{E3}$.

The second blue light LB2 has the wavelength range of 460 to 500 nm and lies between the second isosbestic wavelength $\lambda_{E2}$ and the third isosbestic wavelength $\lambda_{E3}$. The wavelength range of the second blue light LB2 does not include any of the isosbestic wavelengths, so that the difference between the absorption coefficient A1 of oxyhemoglobin and the absorption coefficient A2 of deoxyhemoglobin is large. Therefore the second blue light LB2 is suitable for the measurement light.

On the other hand, the first blue light LB1 has the wavelength range of 420 to 460 nm and includes the second isosbestic wavelength $\lambda_{E2}$, so that the first blue light LB1 is not suitable for the measurement light. However, the first blue light LB1 has the wavelength range that includes a peak wavelength $\lambda_{P1}$, at which the absorption coefficient A1 of oxyhemoglobin is at its peak, and a peak wavelength $\lambda_{P2}$, at which the absorption coefficient A2 of deoxyhemoglobin is at its peak, and is likely to be absorbed by the oxyhemoglobin and the deoxyhemoglobin. Therefore the first blue light LB1 contributes to the improvement of the contrast of the surface blood vessels in the image.

In the oxygen saturation mode, the imaging controller 40 receives a synchronization signal from the light source controller 21 (or inputs a synchronization signal to the light source controller 21). Thereby the imaging controller 40 synchronizes the imaging operation of the image sensor 34 with each of emission period of the normal light and emission period of the measurement light. To be more specific, in a first emission period, in which the normal light is emitted from the light source unit 20, the imaging controller 40 allows the image sensor 34 to take an image of the object irradiated with the normal light and to output the B2 image signal, the G2 image signal, and the R2 image signal. In a second emission period, in which the measurement light is emitted from the light source unit 20, the imaging controller 40 allows the image sensor 34 to take an image of the object irradiated with the measurement light and to output the B3 image signal.

Figure 15:
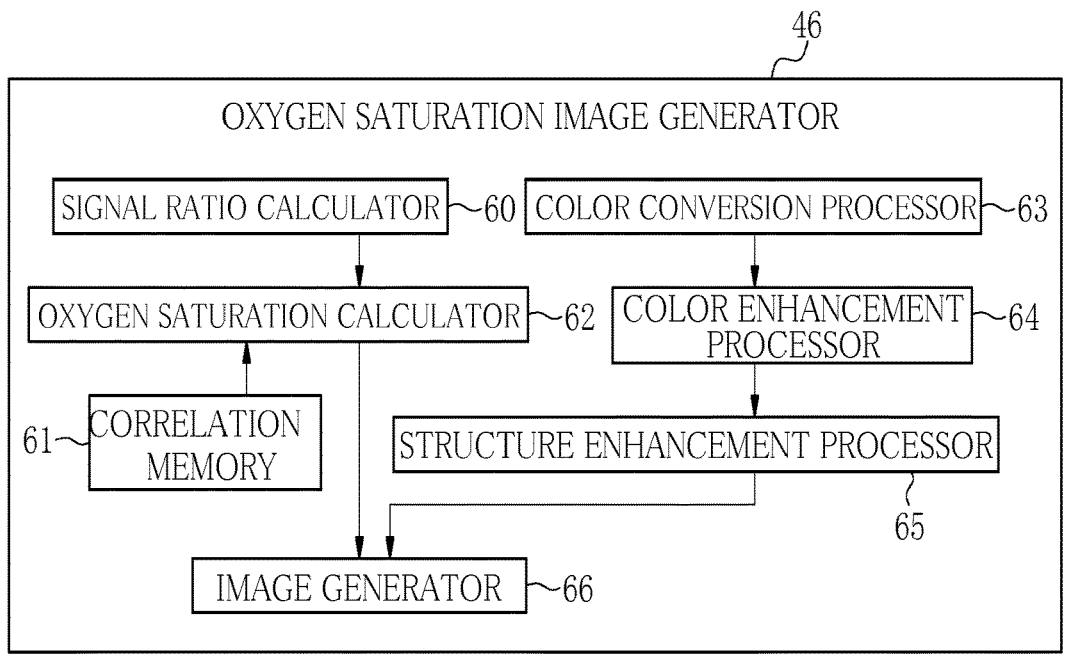
FIG. 15 is a block diagram illustrating functions of an oxygen saturation image generator.

In FIG. 15, the oxygen saturation image generator 46 comprises a signal ratio calculator 60, a correlation memory 61, an oxygen saturation calculator 62, a color conversion processor 63, a color enhancement processor 64, a structure enhancement processor 65, and an image generator 66.

The signal ratio calculator 60 calculates a signal ratio that is used by the oxygen saturation calculator 62 to calculate the oxygen saturation level. To be more specific, the signal ratio calculator 60 calculates a ratio (hereinafter referred to as the first signal ratio B3/G2) between the B3 image signal and the G2 image signal, for each pixel. The B3 image signal is obtained by imaging the object in the second emission mode. The G2 image signal is obtained by imaging the object in the first emission mode. The signal ratio calculator 60 also calculates a ratio (hereinafter referred to as the second signal ratio R2/G2) between the R2 image signal and G2 image signal, which are obtained by imaging the object in the first emission mode, for each pixel.

Figure 16:
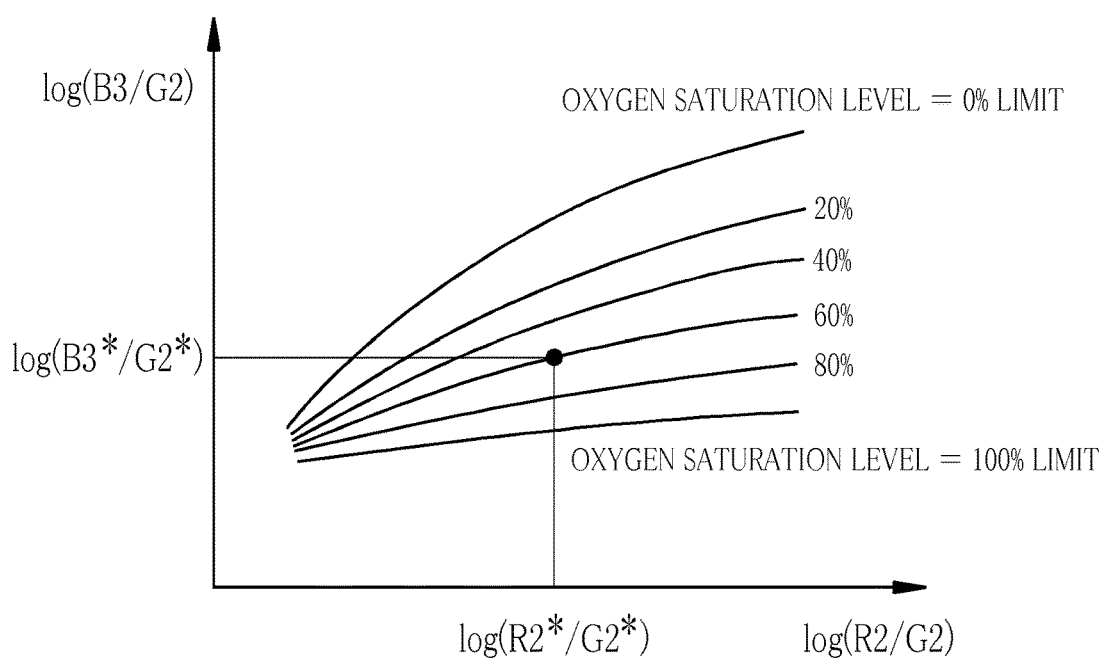
FIG. 16 is a graph illustrating a correlation between signal ratio and oxygen saturation level.

The correlation memory 61 stores a correlation between each signal ratio calculated by the signal ratio calculator 60 and the corresponding oxygen saturation level. The correlation is stored in a form of a two-dimensional table that defines contour lines (or isolines) of the oxygen saturation levels in a two-dimensional space (see FIG. 16). The positions and shapes of the contour lines with respect to the signal ratios are obtained in advance based on physical simulations of light scattering. An interval between the contour lines varies with the second signal ratio R2/G2, which represents the blood volume. Note that the correlation between the signal ratio and the oxygen saturation level is stored in log scale.

The correlation is closely related to absorption characteristics (see FIG. 14) and light scattering characteristics of the oxyhemoglobin and the deoxyhemoglobin. It is easy to obtain the information of the oxygen saturation level with the use of the second blue light LB2 in the wavelength range in which the difference between the absorption coefficient of oxyhemoglobin and the absorption coefficient of deoxyhemoglobin is large. However, the B3 image signal obtained from the second blue light LB2 is highly dependent not only on the oxygen saturation level but also on the blood volume. For this reason, the oxygen saturation level is calculated accurately by using the second signal ratio R2/G2 in addition to the B3 image signal. The second signal ratio R2/G2 is obtained from the G2 image signal, which varies depending mostly on the blood volume, and the R2 image signal, which has low dependence on the oxygen saturation level and the blood volume.

The oxygen saturation calculator 62 consults the correlation stored in the correlation memory 61 and calculates the oxygen saturation level that corresponds to the first signal ratio B3/G2 and the second signal ratio R2/G2, which are calculated by the signal ratio calculator 60. For example, in the case of the first signal ratio B3*/G2* and the second signal ratio R2*/G2* (see FIG. 16), the oxygen saturation level calculated is "60%".

Note that it is very rare that the calculated first signal ratio B3/G2 or the calculated second signal ratio R2/G2 has an extremely large or small value. To be more specific, in FIG. 16, it is very rare that the coordinates represented by the first signal ratio B3/G2 and the second signal ratio R2/G2 is greater than the lower limit contour line, which indicates 0% oxygen saturation level, or less than the upper limit contour line, which indicates 100% oxygen saturation level. However, as a precaution, the oxygen saturation calculator 62 outputs that the oxygen saturation level is 0% in case where the calculated oxygen saturation level is less than 0% and outputs that the oxygen saturation is 100% in case where the calculated oxygen saturation level exceeds 100%.

The oxygen saturation image generator 46 calculates the oxygen saturation level with the use of the signal ratio calculator 60, the correlation memory 61, and the oxygen saturation calculator 62 as described above. The oxygen saturation image generator 46 also produces an image (hereinafter referred to as the base image), from which the oxygen saturation image is produced, with the use of the color conversion processor 63, the color enhancement processor 64, and the structure enhancement processor 65.

The color conversion processor 63 performs a color conversion process on the B2 image signal, the G2 image signal, and the R2 image signal, which are obtained by imaging the object in the first emission mode, through 3×3 matrix processing, a tone conversion process, a three-dimensional LUT process, and the like. After the color conversion process, the color enhancement processor 64 performs the color enhancement process on the B2 image signal, the G2 image signal, and the R2 image signal. After the color enhancement process, the structure enhancement processor 65 performs the structure enhancement process on the B2 image signal, the G2 image signal, and the R2 image signal. The structure enhancement process enhances the structure (e.g. the surface blood vessels and the pit patterns) of the object. In other words, the base image is produced from the B2 image signal, the G2 image signal, and the R2 image signal that have been subjected to the various types of image processing similar to those performed by the normal image generator 45.

The image generator 66 produces the oxygen saturation image, which shows the oxygen saturation levels of the object, with the use of the B2 image signal, the G2 image signal, and the R2 image signal that have been subjected to the above-described various types of image processing and the oxygen saturation level calculated by the oxygen saturation calculator 62. To be more specific, the image generator 66 multiplies each of the B2 image signal, the G2 image signal, and the R2 image signal by a gain in accordance with the oxygen saturation level, for each pixel (hereinafter referred to as the gain process).

For example, with regard to the pixel with the oxygen saturation level of 60% or more, the image generator 66 sets the gain for the B2 image signal, the G2 image signal, and the R2 image signal to "1". This means that the image generator 66 does not perform the gain process. With regard to the pixel with the oxygen saturation level of less than 60%, the gain for the B2 image signal is set to be less than "1" and the gain for the G2 image signal and the R2 image signal is set to be greater than or equal to "1" in accordance with the oxygen saturation level. The oxygen saturation image is produced from the B2 image signal, the G2 image signal, and the R2 image signal that are obtained after the gain process. For this reason, in the oxygen saturation image, the pixel with a high oxygen level (the pixel with the oxygen saturation level of 60 to 100%) represents a color similar to that of the normal image. The pixel with a low oxygen level (the pixel with the oxygen saturation level of less than 60%) represents a color (pseudo color) different from that of the normal image.

In this embodiment, note that the image generator 66 performs the gain process, in accordance with the oxygen saturation level, only on the pixels with low oxygen levels. Instead, the gain process may also be performed on the pixels with high oxygen levels. Thereby the entire oxygen saturation image is displayed in pseudo-colors. The reference value of the oxygen saturation level that separates the high and low oxygen levels is set to 60% by way of example. The reference value may be changed as necessary.

Figure 17:
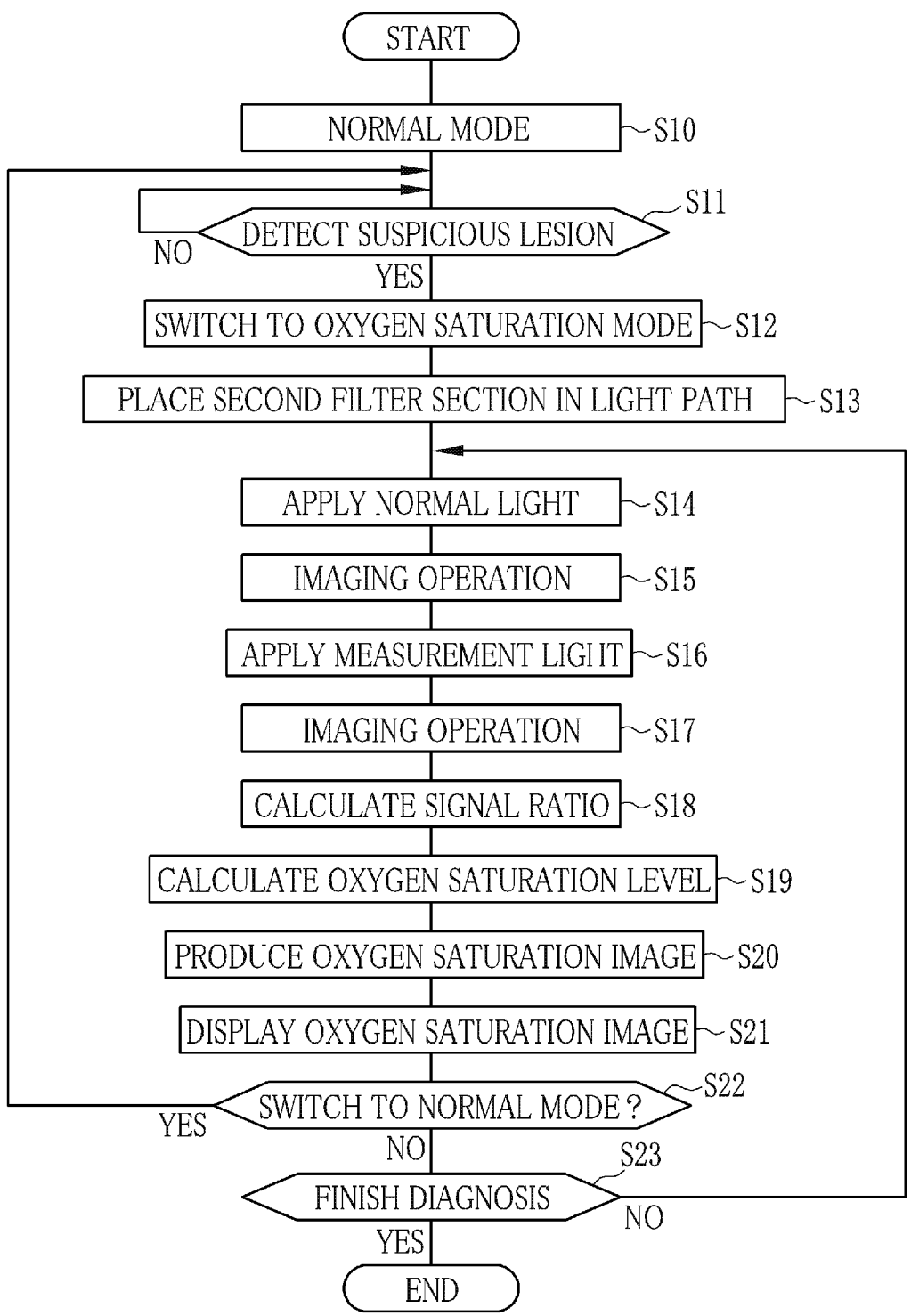
FIG. 17 is a flowchart illustrating an operation of the endoscope system.

Hereinafter, referring to a flowchart illustrated in FIG. 17, an operation of this embodiment is described. First, in the normal mode, screening from distant view is performed (S10). In the normal mode, the first filter section 57a of the optical filter 57 is placed in the light path of the blue light LB. In a case where a suspicious lesion, being a site suspected to be a lesion such as a brownish area or redness, is detected during the screening (S11), the zoom operating section 13b is operated to zoom (magnify) the object including the suspicious lesion. Also, the mode SW 13a is operated to switch from the normal mode to the oxygen saturation mode (S12).

Upon the observation mode is switched to the oxygen saturation mode, the light source controller 21 places the second filter section 57b of the optical filter 57 in the light path of the blue light LB (S13). The light source controller 21 turns on all of the V-LED 50a, the B-LED 50b, the G-LED 50c, and the R-LED 50d. Thereby the normal light, which is composed of the violet light LV, the second blue light LB2, the green light LG, and the red light LR, is applied to the object (S14). The image sensor 34 takes an image of the object irradiated with the normal light and outputs the B2 image signal, the G2 image signal, and the R2 image signal (S15).

Thereafter, the light source controller 21 automatically switches the emission mode and turns on only the B-LED 50b. Thereby the measurement light composed of the second blue light LB2 is applied to the object (S16). The image sensor 34 takes an image of the object irradiated with the measurement light and outputs the B3 image signal (S17).

Upon obtaining the B2 image signal, the G2 image signal, and the R2 image signal in the first emission mode and the B3 image signal in the second emission mode, the oxygen saturation image generator 46 calculates the first signal ratio B3/G2 and the second signal ratio R2/G2 (S18) with the use of the signal ratio calculator 60 and calculates the oxygen saturation level (S19) with the use of the oxygen saturation calculator 62. Based on the B2 image signal, the G2 image signal, and the R2 image signal, the oxygen saturation image generator 46 generates the base image, from which the oxygen saturation image is produced, with the use of the color conversion processor 63, the color enhancement processor 64, and the structure enhancement processor 65.

The image generator 66 multiplies each of the B2 image signal, the G2 image signal, and the R2 image signal that have been subjected to the various types of image processing by a gain in accordance with the oxygen saturation level, thereby producing the oxygen saturation image (S20). The oxygen saturation image is converted by the video signal generator 47 into a video signal and then displayed on the monitor 18 (S21).

The steps S14 to S21 in the oxygen saturation mode are repeated until the oxygen saturation mode is switched to the normal mode (YES in S22) or the diagnosis is finished (YES in S23). Note that the above-described steps are described by way of example. The observation and the diagnosis in the oxygen saturation mode may be performed in a different manner. For example, in the above-described steps, the object is observed in a close view in the oxygen saturation mode by way of example. The oxygen saturation mode may be chosen to perform the screening or the like from the distant view. In the above embodiment, an image of the object is taken in the second emission mode after an image of the object is taken in the first emission mode. Alternatively, the image is taken in the first emission mode after the image is taken in the second emission mode.

As described above, the first blue light LB1 and the second blue light LB2 are selectively generated based on the blue light LB emitted from the B-LED 50b, allowing various types of observation (or examinations) and diagnoses. In the normal mode, the first blue light LB1 that is generated by reducing the intensity of the blue light LB in the wavelength range of greater than or equal to 460 nm is used. Thereby, a blue image component with high image quality and improved blood vessel contrast is obtained. In the oxygen saturation mode, the second blue light LB2 that is generated by reducing the intensity of the blue light LB in the wavelength range of less than or equal to 460 nm is used as the measurement light. Thereby the oxygen saturation level is calculated with high accuracy.

Note that, in the first embodiment, the peak wavelength of the blue light LB is 460 nm, but not limited thereto. It is preferred that the peak wavelength of the blue light LB is greater than or equal to 450 nm. It is more preferred that the peak wavelength of the blue light LB is within a range of 450 to 460 nm.

It is preferred to reduce the intensity of the blue light LB in the wavelength range of at least greater than or equal to the peak wavelength of the blue light LB to generate the first blue light LB1. It is preferred to reduce the intensity of the blue light LB in the wavelength range of at least less than or equal to the peak wavelength of the blue light LB to generate the second blue light LB2. In other words, the threshold value S1 of the first filter section 57a may be less than the peak wavelength of the blue light LB. The threshold value S2 of the second filter section 57b may be greater than the peak wavelength of the blue light LB.

In the above embodiment, the band limiter 53 allows the filter moving mechanism 58 to linearly move or slide the optical filter 57, thereby switching the filter (the first filter section 57a or the second filter section 57b) placed in the light path of the blue light LB. Note that the optical filter 57 may be a rotary plate formed with the semicircular first filter section 57a and the semicircular second filter section 57b. The filter section to be placed in the light path of the blue light LB is switched by rotating the rotary plate.

In the above embodiment, the first to third DMs 55a to 55c with the optical characteristics illustrated in FIGS. 8 to 10 are used but not limited thereto. The relationship between the optical characteristics (transmissive and reflective characteristics) of each of the first to third DMs 55a to 55c may be reversed.

Second Embodiment

In the first embodiment, the band limiter 53, which comprises the optical filter 57 and the filter moving mechanism 58, selectively generates the first blue light LB1 and the second blue light LB2. In a second embodiment, a band limiter comprises dichroic mirrors, a light shielding plate, and a light shielding plate moving mechanism.

Figure 18:
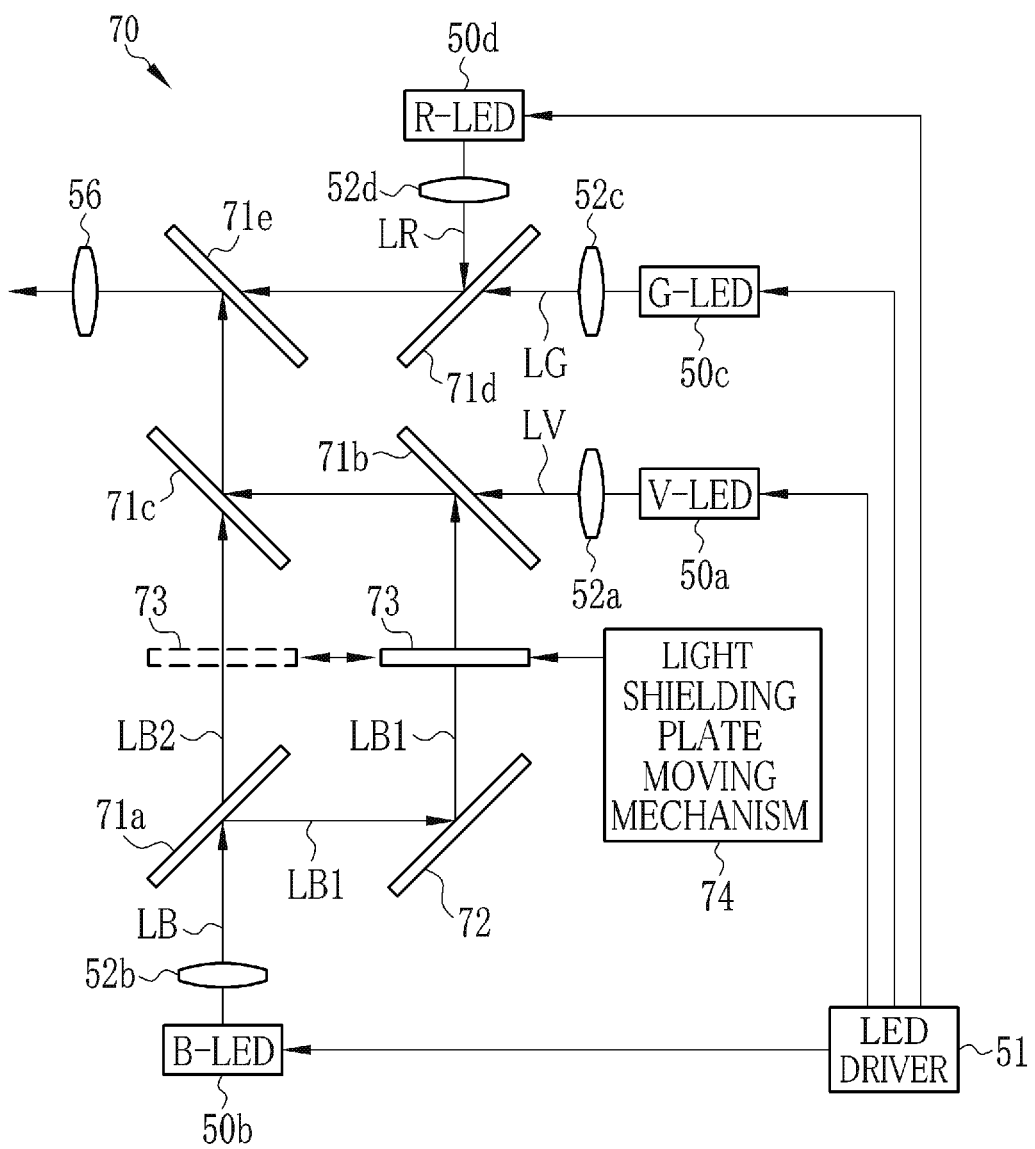
FIG. 18 is a schematic view illustrating a light source unit of a second embodiment.

In FIG. 18, a light source unit 70 of the second embodiment comprises the V-LED 50a, the B-LED 50b, the G-LED 50c, the R-LED 50d, the LED driver 51, and the first to fourth collimator lenses 52a to 52d, and the condenser lens 56. These are the same as those of the first embodiment, so that the descriptions thereof are omitted. The light source unit 70 also comprises first to fifth dichroic mirrors (DMs) 71a to 71e, a mirror 72, a light shielding plate 73, and a light shielding plate moving mechanism 74.

Figure 19:
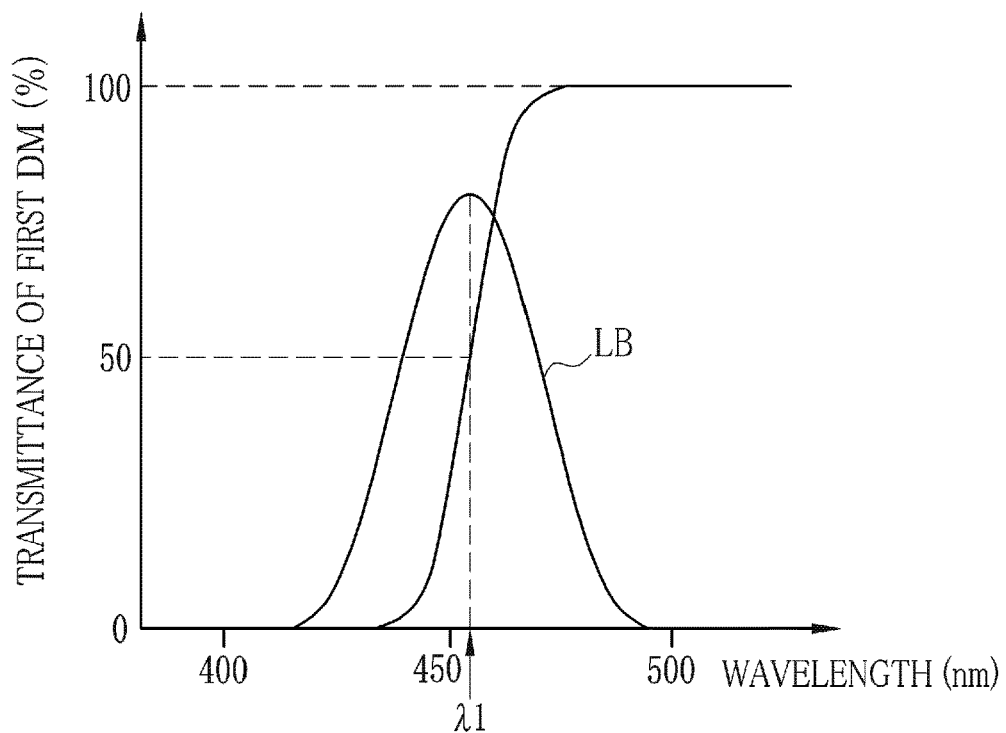
FIG. 19 is a graph illustrating an optical characteristic of a first dichroic mirror of the second embodiment.

The first DM 71a is disposed in the light path of the blue light LB from the B-LED 50b such that the blue light LB is incident on the first DM 71a at the angle of 45°. As illustrated in FIG. 19, the first DM 71a has a threshold value $\lambda 1$ of approximately 460 nm, and passes the light of wavelengths longer than the threshold value $\lambda 1$ and reflects the light of wavelengths shorter than the threshold value $\lambda 1$. In the strict sense, the transmittance and the reflectance of the first DM 71a do not change from 0% to 100% at the threshold value $\lambda 1$. Actually, the transmittance and the reflectance change from 0% to 100% within in the order of 50 nm. For this reason, the wavelength at which the transmittance and the reflectance are approximately 50% is defined as the threshold value $\lambda 1$.

Figure 20:
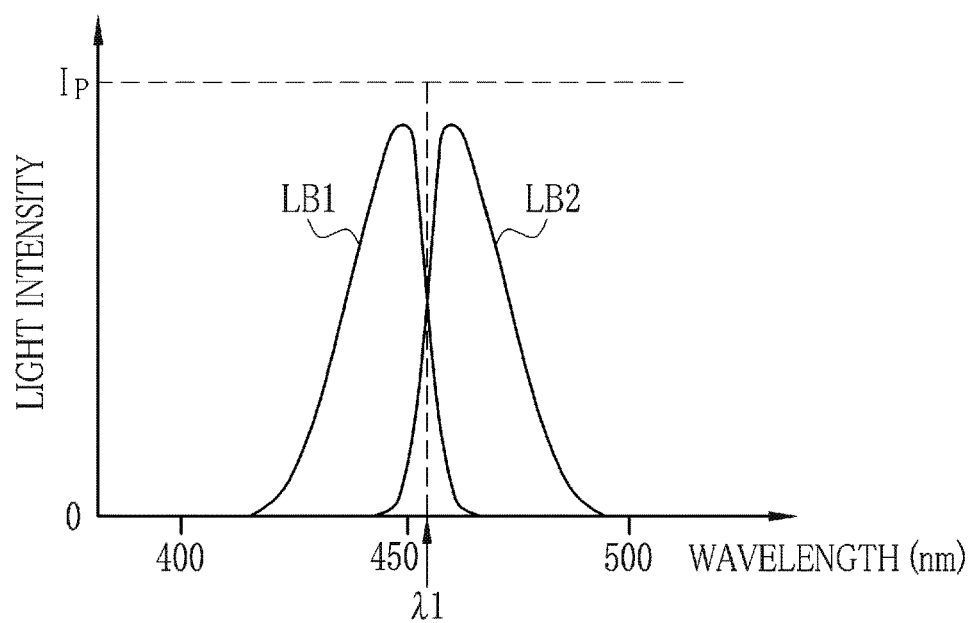
FIG. 20 is a graph illustrating optical spectrums of first blue light and second blue light.

The threshold value $\lambda 1$ of the first DM 71a substantially equals the peak wavelength 460 nm of the blue light LB. As illustrated in FIG. 20, the first DM 71a separates the blue light LB into the first blue light LB1 and the second blue light LB2. The first blue light LB1 is a component of the blue light LB reflected by the first DM 71a. The wavelength range of the first blue light LB1 is less than or equal to approximately 460 nm. The second blue light LB2 is a component of the blue light LB passing through the first DM 71a. The wavelength range of the second blue light LB2 is greater than or equal to approximately 460 nm.

The wavelength range of the first blue light LB1 partly overlaps the wavelength range of the second blue light LB2 because the first DM 71a has the wavelength width within which the transmittance and the reflectance change from 0% to 100%. Each of the peak intensities of the first blue light LB1 and the second blue light LB2 is less than the peak intensity $I_P$ of the blue light LB.

The first DM 71a reflects the first blue light LB1 in a direction orthogonal to the light path of the blue light LB. The mirror 72 is disposed such that first blue light LB1 is incident at the angle of 45°. The mirror 72 reflects the first blue light LB1 to change its light path by 90°. Thereby, the light path of the first blue light LB1 is substantially parallel to the light path of the second blue light LB2.

The light shielding plate moving mechanism 74 linearly moves or slides the light shielding plate 73 between a first position for blocking the light path of the first blue light LB1 and a second position for blocking the light path of the second blue light LB2. Thereby the light shielding plate 73 blocks one of the first blue light LB1 and the second blue light LB2.

The second DM 71b is disposed such that the first blue light LB1 is incident on one of its surfaces at the angle of 45° and the violet light LV from the V-LED 50a is incident on the other surface at the angle of 45°. The second DM 71b has a threshold value $\lambda 2$ of approximately 425 nm, and passes the light of wavelengths shorter than the threshold value $\lambda 2$ and reflects the light of wavelengths longer than the threshold value $\lambda 2$. Thereby, the second DM 71b combines the light path of the first blue light LB1 with the light path of the violet light LV.

The third DM 71c is disposed such that the second blue light LB2 is incident on one of its surfaces at 45° and the first blue light LB1 and the violet light LV that emanate from the second DM 71b are incident on the other surface at 45°. The third DM 71c has the same optical characteristics as those of the first DM 71a (see FIG. 19). The third DM 71c passes the second blue light LB2 and reflects the first blue light LB1 and the violet light LV. Thus the third DM 71c combines the light path of the second blue light LB2 with the light path of the first blue light LB1 and the light path of the violet light LV.

The fourth DM 71*d* has the same optical characteristics as those of the second DM 55*b* of the first embodiment (see FIG. 9). The fourth DM 71*d* combines the light path of the green light LG from the G-LED 50*c* with the light path of the red light LR from the R-LED 50*d*. The fifth DM 71*e* has the same optical characteristics as those of the third DM 55*c* of the first embodiment (see FIG. 10). The fifth DM 71*e* combines the light paths combined together by the third DM 71*c* with the light paths combined together by the fourth DM 71*d*. The light from the fifth DM 71*e* is collected by the condenser lens 56 and then incident on the end of the light guide 23.

In the normal mode in this embodiment, the light source controller 21 controls the light shielding plate moving mechanism 74 to place the light shielding plate 73 in the light path of the second blue light LB2 and controls the LED driver 51 to turn on all of the V-LED 50*a*, the B-LED 50*b*, the G-LED 50*c*, and the R-LED 50*d*. Thereby, the second blue light LB2 is blocked by the light shielding plate 73, so that the first illumination light having the light intensity spectrum illustrated in FIG. 11 is emitted from the light source unit 70.

In the first emission mode of the oxygen saturation mode, the light source controller 21 controls the light shielding plate moving mechanism 74 to place the light shielding plate 73 in the light path of the first blue light LB1 and controls the LED driver 51 to turn on all of the V-LED 50*a*, the B-LED 50*b*, the G-LED 50*c*, and the R-LED 50*d*. Thereby, the first blue light LB1 is blocked by the light shielding plate 73, so that the normal light having the light intensity spectrum illustrated in FIG. 12 is emitted from the light source unit 70.

In the second emission mode of the oxygen saturation mode, the light source controller 21 controls the LED driver 51 to turn on only the B-LED 50*b* while the light shielding plate 73 is placed in the light path of the first blue light LB1. Thereby the first blue light LB1 is blocked by the light shielding plate 73, so that the measurement light having the light intensity spectrum illustrated in FIG. 13 is emitted from the light source unit 70.

In the second embodiment, the band limiter comprises the first DM 71*a*, the light shielding plate 73, and the light shielding plate moving mechanism 74 as described above. Other than those, the configuration and the operation of the second embodiment are similar to those of the first embodiment.

Note that in the second embodiment, the first DM 71*a* and the third DM 71*c* have the optical characteristics illustrated in FIG. 19 but they are not limited thereto. The relationship between the transmissive and reflective characteristics of each of the first and third DMs 71*a* to 71*c* may be reversed.

In the second embodiment, the sliding type light shielding plate 73 is used. Instead, a rotary type light shielding plate (rotary plate) may be used. For example, one of semicircular portions of the rotary plate is used as the light shielding section. The other semicircular portion of the rotary plate is an opening. The rotary plate is placed such that each of the light shielding section and the opening passes through each of the light paths of the first and second blue light LB1 and LB2 as the rotary plate is rotated.

Figure 21:
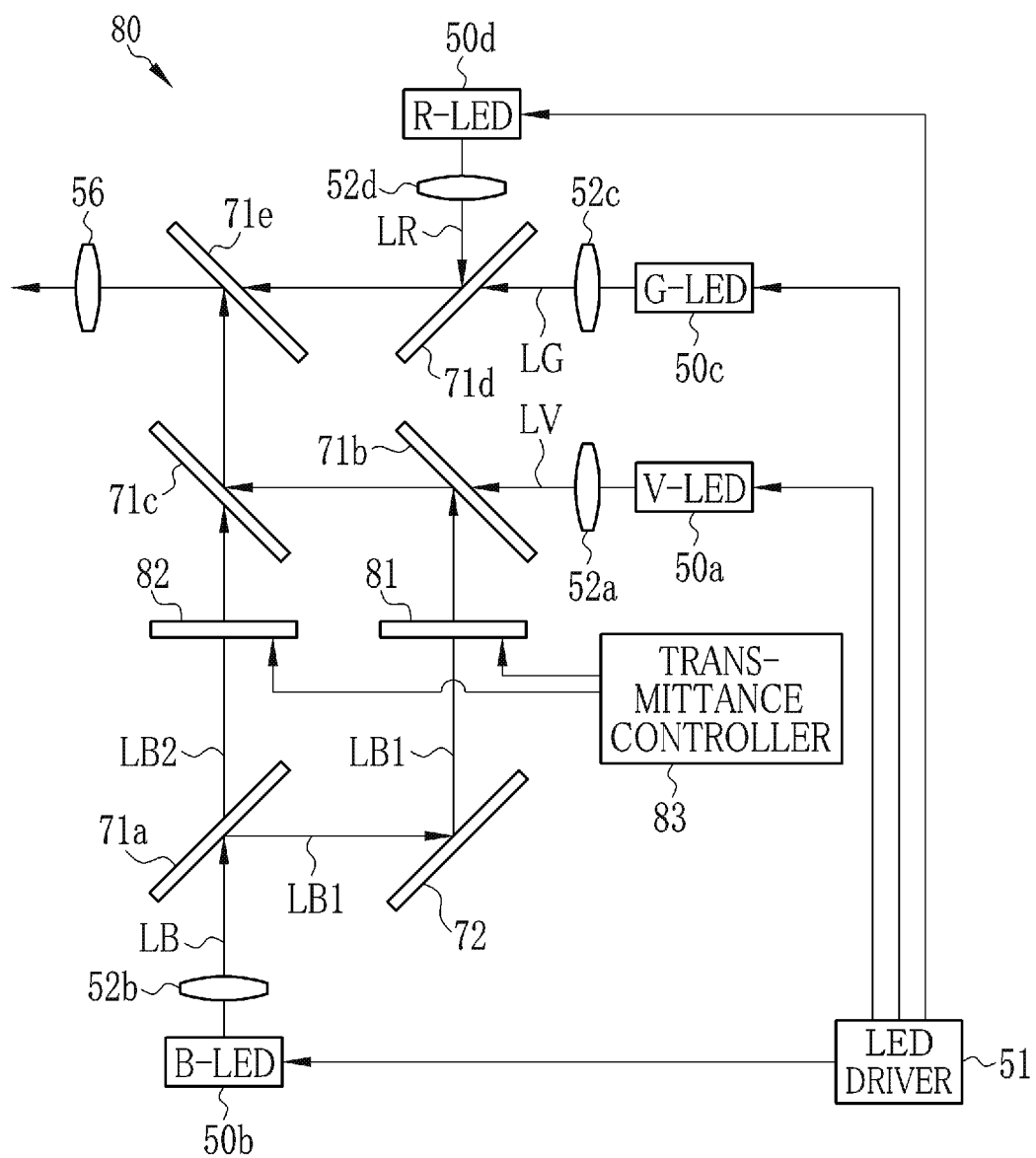
FIG. 21 is a schematic view illustrating a modified example of the light source unit of the second embodiment.

In the second embodiment, the light shielding plate 73 and the light shielding plate moving mechanism 74 constitute a so-called mechanical shutter. Instead of the mechanical shutter, a transmittance changing unit (e.g. a liquid crystal shutter or the like) that electrically changes the transmittance may be used. In FIG. 21, a light source unit 80 comprises a first transmittance changing unit 81, a second transmittance changing unit 82, and a transmittance controller 83, in place of the light shielding plate 73 and the light shielding plate moving mechanism 74 of the light source unit 70 of the second embodiment.

The first transmittance changing unit 81 is disposed in the light path of the first blue light LB1. The second transmittance changing unit 82 is disposed in the light path of the second blue light LB2. The transmittance controller 83 controls each of the transmittance of the first transmittance changing unit 81 and the transmittance of the second transmittance changing unit 82.

In the normal mode, the light source controller 21 controls the transmittance controller 83 to set the transmittance of the first transmittance changing unit 81 to approximately 100% and the transmittance of the second transmittance changing unit 82 to approximately 0% and controls the LED driver 51 to turn on all of the V-LED 50*a*, the B-LED 50*b*, the G-LED 50*c*, and the R-LED 50*d*. Thereby the second transmittance changing unit 82 reduces the intensity of the second blue light LB2, so that the first illumination light having the light intensity spectrum illustrated in FIG. 11 is emitted from the light source unit 80.

In the first emission mode of the oxygen saturation mode, the light source controller 21 controls the transmittance controller 83 to set the transmittance of the first transmittance changing unit 81 to approximately 0% and the transmittance of the second transmittance changing unit 82 to approximately 100% and controls the LED driver 51 to turn on all of the V-LED 50*a*, the B-LED 50*b*, the G-LED 50*c*, and the R-LED 50*d*. Thereby the first transmittance changing unit 81 reduces the intensity of the first blue light LB1, so that the normal light having the light intensity spectrum illustrated in FIG. 12 is emitted from the light source unit 80.

In the second emission mode of the oxygen saturation mode, the light source controller 21 controls the LED driver 51 to turn on only the B-LED 50*b* while maintaining the transmittance of the first transmittance changing unit 81 at approximately 0% and the transmittance of the second transmittance changing unit 82 at approximately 100%. Thereby the first transmittance changing unit 81 reduces the intensity of the first blue light LB1, so that the measurement light having the light intensity spectrum illustrated in FIG. 13 is emitted from the light source unit 80.

In the above embodiments, the image sensor 34 is a primary color image sensor. Instead, a complementary color image sensor with complementary color filters of C (cyan), M (magenta), Y (yellow), and G (green) may be used. The complementary color image sensor outputs CMYG image signals, which are converted into the RGB image signals through a color conversion process. A monochrome image sensor may be used instead. In this case, the V-LED 50*a*, the B-LED 50*b*, the G-LED 50*c*, and the R-LED 50*d* are turned on in a time-division manner. In this case, note that the V-LED 50*a* and the B-LED 50*b* may be turned on simultaneously.

Figure 22:
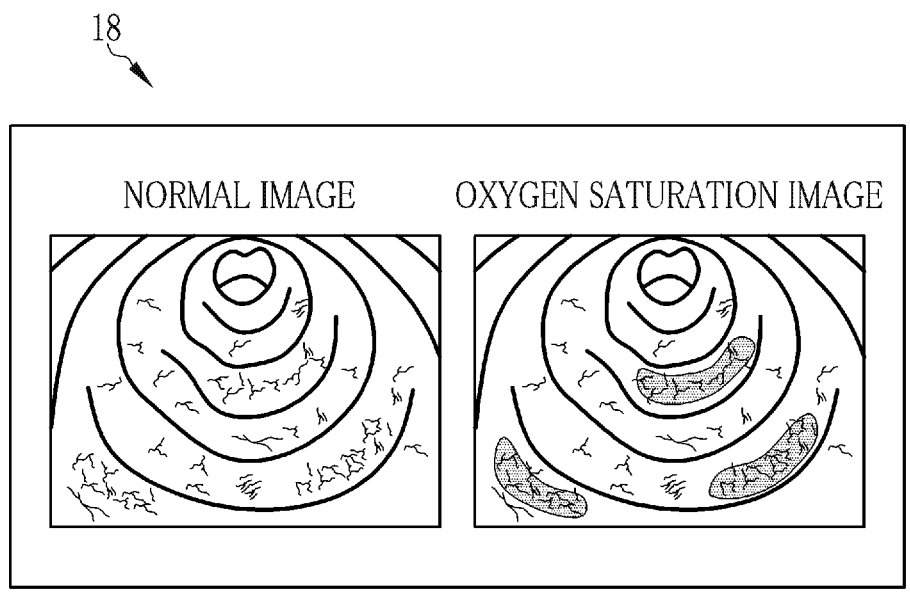
FIG. 22 illustrates an example of a display of images on a monitor.

In the above embodiments, the monitor 18 displays a normal image in the normal mode and an oxygen saturation image in the oxygen saturation mode. As illustrated in FIG. 22, the monitor 18 may display the normal image (the first image) in addition to the oxygen saturation image (the second image) in the oxygen saturation mode. The normal image and the oxygen saturation image are simultaneously displayed on the monitor 18, allowing viewing of the portions of the normal image (original image) corresponding to the portions of the low oxygen saturation image colored differently in accordance with the oxygen saturation levels.

In the second emission mode in the above embodiments, the B-LED 50*b* is turned on while the V-LED 50*a*, the G-LED 50*c*, and the R-LED 50*d* are turned off. Instead of turning them off, the amounts of the light may be reduced to extremely small values to the extent that substantially only the blue light LB is emitted. Thus, occurrence of switching noise of the LEDs is prevented by not completely turning off the V-LED 50*a*, the G-LED 50*c*, and the R-LED 50*d*.

In the above embodiments, the normal light having the light intensity spectrum shown in FIG. 12 is used as the illumination light in the first emission mode of the oxygen saturation mode. Instead, the normal light having the light intensity spectrum shown in FIG. 11 may be used. In this case, the first blue light LB1 is generated in the first emission mode. The second blue light LB2 is generated in the second emission mode.

In a case where the light source unit 20 (see FIG. 4) of the first embodiment is used, the optical filter 57 is moved in accordance with switching the emission mode. To be more specific, in the first emission mode, the first filter section 57*a* is placed in the light path of the blue light LB. Thereby the first blue light LB1 is generated. In the second emission mode, the second filter section 57*b* is placed in the light path of the blue light LB. Thereby the second blue light LB2 is generated.

In a case where the light source unit 70 (see FIG. 18) of the second embodiment is used, the light shielding plate 73 is moved in accordance with switching the emission mode. To be more specific, in the first emission mode, the light shielding plate 73 is placed in the light path of the second blue light LB2 to generate the first blue light LB1. In the second emission mode, the light shielding plate 73 is placed in the light path of the first blue light LB1 to generate the second blue light LB2.

In a case where the light source unit 80 (see FIG. 21) is used, the transmittance of the first transmittance changing unit 81 and the transmittance of the second transmittance changing unit 82 are changed in accordance with switching the emission mode. To be more specific, in the first emission mode, the transmittance of the first transmittance changing unit 81 is set to approximately 100% and the transmittance of the second transmittance changing unit 82 is set to approximately 0%. Thereby the first blue light LB1 is generated. In the second emission mode, the transmittance of the first transmittance changing unit 81 is set to approximately 0% and the transmittance of the second transmittance changing unit 82 is set to approximately 100%. Thereby the second blue light LB2 is generated. The transmittance of the first transmittance changing unit 81 and the transmittance of the second transmittance changing unit 82 are controlled electrically, so that the transmittance is switched instantly. Thus, the emission mode is switched at a high switching rate, resulting in a high frame rate.

In the first emission mode, the first blue light LB1 is generated, so that the base image of the oxygen saturation image is produced using the normal light with the intensity in the wavelength range of 460 to 500 nm reduced. Thereby the contrast of the fine structure such as the surface blood vessels and the pit patterns is improved in the image. The oxygen saturation image is produced based on the base image with high image quality and improved blood vessel contrast.

In each of the first and second embodiments, the endoscope system is provided with the normal mode and the oxygen saturation mode. In addition, it is preferred that the endoscope system is provided with a blue-light mode in which the intensity of a short wavelength component of the first illumination light is enhanced. In the blue-light mode, the light emission intensities of the V-LED 50*a* and the B-LED 50*b* are increased to be higher than those in the normal mode, to generate the first illumination light in which the intensities of the short wavelength components are increased. Other than that, the configuration is similar to those of the above embodiments. The violet light LV and the first blue light LB1 contained in the first illumination light are likely to be absorbed by hemoglobin in the blood vessels in the mucosal surface. Thereby, the surface blood vessels and the pit patterns are enhanced in an image.

In the above embodiments, the light source device 14 and the processor device 16 are provided separately. Alternatively, the light source device and the processor device may be provided integrally.

Figure 23:
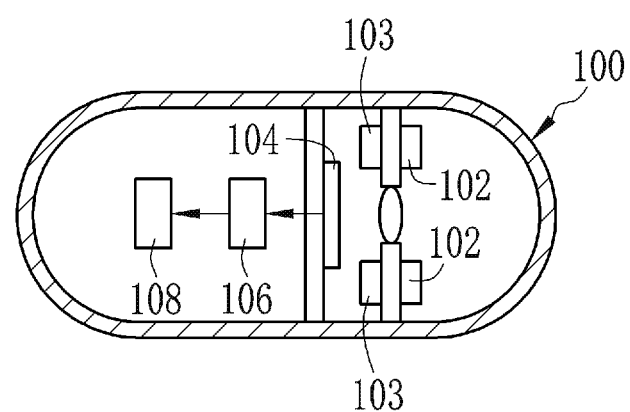
FIG. 23 is a schematic view illustrating a capsule endoscope.

In the above embodiments, an aspect of the present invention is performed by using the endoscope system 10 comprising the endoscope 12 provided with the image sensor 34. The observation or examination is performed by inserting the endoscope 12 into a body cavity. The present invention is also suitable for a capsule endoscope system. For example, as illustrated in FIG. 23, the capsule endoscope system comprises at least a capsule endoscope 100 and a processor device (not shown).

The capsule endoscope 100 comprises a light source 102, a light source controller 103, an image sensor 104, an oxygen saturation image generator 106, and a transmission/reception antenna 108. The light source 102 comprises a V-LED that emits the violet light LV, a B-LED that emits the blue light LB, a G-LED that emits the green light LG, and an R-LED that emits the red light LR, and a band limiter for selectively generating the first blue light LB1 and the second blue light LB2 from the blue light LB. For example, the light source 102 corresponds to the light source unit of the above embodiment.

The light source controller 103 controls the light source 102, in a manner similar to the light source controller 21 of each of the above embodiments. The light source controller 103 is wirelessly communicable with the processor device of the capsule endoscope system through the transmission/reception antenna 108. The processor device of the capsule endoscope system is substantially similar to the processor device 16 of each of the above embodiments, except that the oxygen saturation image generator 106, which corresponds to the oxygen saturation image generator 46, is provided in the capsule endoscope 100. The oxygen saturation image produced by the oxygen saturation image generator 106 is transmitted to the processor device through the transmission/reception antenna 108. The configuration of the image sensor 104 is similar to that of the image sensor 34 of each of the above embodiments.

Various changes and modifications are possible in the present invention and may be understood to be within the present invention.

What is claimed is:

1. An endoscope system comprising:
   a light source device including:
   a blue light source for emitting blue light, a peak wavelength of the blue light being within a range of 450 nm to 460 nm;
   an electric signal processor for controlling the blue light source; and
   a band limiter controlled by an electric signal from the electric signal processor, the band limiter configured to selectively generate first blue light and second blue light from the blue light emitted from the blue light source, the band limiter reducing intensity of the blue light in a wavelength range of greater than the peak wavelength of the blue light and transmitting all other wavelengths of the blue light to generate the first blue light, the band limiter reducing intensity of the blue light in a wavelength range of less than the peak wavelength of the blue light and transmitting all other wavelengths of the blue light to generate the second blue light, wherein the endoscope system is configured to execute a normal observation using an image in which contrast of blood vessels is enhanced, and an observation of an oxygen saturation level, and wherein the electric signal processor is configured to control the blue light source and the band limiter, to generate the first blue light as first illumination light in the normal observation, and to generate the second blue light as second illumination light in the observation of the oxygen saturation level.

2. The endoscope system according to claim 1, wherein the band limiter comprises an optical filter and a filter moving mechanism, and the optical filter comprises a first filter section for generating the first blue light from the blue light and a second filter section for generating the second blue light from the blue light, and the filter moving mechanism moves the optical filter to place one of the first and second filter sections in a light path of the blue light.

3. The endoscope system according to claim 1, wherein the band limiter comprises a dichroic mirror for separating the blue light into the first blue light and the second blue light, a light shielding plate for blocking the blue light, and a light shielding plate moving mechanism configured to move the light shielding plate in one of light paths of the first blue light and the second blue light.

4. The endoscope system according to claim 1, wherein the band limiter comprises a dichroic mirror for separating the blue light into the first blue light and the second blue light, a first transmittance changing unit with variable transmittance and for reducing intensity of the first blue light, a second transmittance changing unit with variable transmittance and for reducing intensity of the second blue light, and a transmittance controller for controlling the transmittance of the first transmittance changing unit and the transmittance of the second transmittance changing unit.

5. The endoscope system according to claim 1, further comprising a green light source for emitting green light and a red light source for emitting red light, wherein the light source controller is configured to generate the first illumination light and the second illumination light, and the first illumination light contains the first blue light, the green light, and the red light, and the second illumination light contains the second blue light.

6. The endoscope system according to claim 5, further comprising:

an image sensor configured to image an object of interest irradiated with the first or second illumination light and for outputting an image signal; and an image processing unit for producing a first image based on the image signal obtained by imaging the object of interest irradiated with the first illumination light and for producing a second image based on the image signal obtained by imaging the object of interest irradiated with the second illumination light.

7. The endoscope system according to claim 6, further comprising a display for displaying the first image and the second image, the display displaying the first and second images simultaneously.

8. The endoscope system according to claim 6, wherein the second blue light has a wavelength range in which an absorption coefficient of oxyhemoglobin is greater than an absorption coefficient of deoxyhemoglobin.

9. The endoscope system according to claim 8, wherein the image sensor has blue pixels for receiving the blue light, green pixels for receiving the green light, and red pixels for receiving the red light.

10. The endoscope system according to claim 9, wherein the image processing unit images the object of interest irradiated with the first illumination light and produces the first image based on a first blue image signal outputted from the blue pixels, a first green image signal outputted from the green pixels, and a first red image signal outputted from the red pixels.

11. The endoscope system according to claim 10, wherein the second illumination light is separated into normal light and measurement light, the normal light containing the second blue light, the green light, and the red light, the measurement light being composed of the second blue light, and the image processing unit images the object of interest irradiated with the normal light and produces a base image based on a second blue image signal outputted from the blue pixels, a second green image signal outputted from the green pixels, and a second red image signal outputted from the red pixels, and images the object of interest irradiated with the measurement light and calculates the oxygen saturation level based on a third blue image signal outputted from the blue pixels, and performs image processing of the base image based on the oxygen saturation level to produce the second image.

12. The endoscope system according to claim 9, further comprising a violet light source for emitting violet light to which the blue pixels are sensitive, wherein the light source controller generates the first illumination light containing the violet light, the first blue light, the green light, and the red light.

13. The endoscope system according to claim 6, wherein the endoscope system is configured to execute a normal mode in which the object of interest is irradiated only with the first illumination light and only the first image is produced.

* * * * *